(12) United States Patent
Jung et al.

(10) Patent No.: US 9,364,480 B2
(45) Date of Patent: Jun. 14, 2016

(54) PHARMACEUTICAL COMPOSITION FOR PREVENTING OR TREATING CANCER, CONTAINING ENOBLOCK AS ACTIVE INGREDIENT

(71) Applicant: GWANGJU INSTITUTE OF SCIENCE AND TECHNOLOGY, Gwangju (KR)

(72) Inventors: Da-Woon Jung, Gwangju (KR); Woong-Hee Kim, Gwangju (KR); Darren Williams, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 0 days.

(21) Appl. No.: 14/437,277

(22) PCT Filed: Oct. 22, 2013

(86) PCT No.: PCT/KR2013/009438
§ 371 (c)(1),
(2) Date: Apr. 21, 2015

(87) PCT Pub. No.: WO2014/065572
PCT Pub. Date: May 1, 2014

(65) Prior Publication Data
US 2015/0246050 A1 Sep. 3, 2015

(30) Foreign Application Priority Data
Oct. 22, 2012 (KR) ......................... 10-2012-0117417

(51) Int. Cl.
*A61K 31/53* (2006.01)

(52) U.S. Cl.
CPC ..................................... *A61K 31/53* (2013.01)

(58) Field of Classification Search
None
See application file for complete search history.

(56) References Cited

U.S. PATENT DOCUMENTS 5,536,722 A 7/1996 Coe et al.

FOREIGN PATENT DOCUMENTS

| EP | 1479397 A1 | 11/2004 |
|---|---|---|
| KR | 10-2012-0011664 A | 2/2012 |
| WO | WO-2012/015249 A2 | 2/2012 |

OTHER PUBLICATIONS

Hörig et al., J. Translational Med. 2:44 (2004).*
Jung et al., "Novel use of fluorescent glucose analogues to identify a new class of triazine-based insulin mimetics possessing useful secondary effects," Mol Biosyst. 7(2):346-58 (2011).
International Search Report for International Application No. PCT/KR2013/009438, dated Feb. 11, 2014 (7 pages).

* cited by examiner

*Primary Examiner* — Michael Barker
(74) *Attorney, Agent, or Firm* — Clark & Elbing LLP; Susan M. Michaud

(57) ABSTRACT

The present invention relates to ENOblock, which is a nonsubstrate analog having an enolase inhibitory activity, and a pharmaceutical composition for preventing or treating cancer or enolase-associated diseases, containing the same. The ENOblock of the present invention directly binds to enolase so as to inhibit an activity thereof, and the inhibition is more effective in hypoxia than in normoxia. In addition, the ENOblock of the present invention inhibits migration, metastasis and invasion of cancer cells. Furthermore, the ENOblock of the present invention induces glucose uptake into cells, down-regulates the expression of PEPCK, and inhibits adipogenesis and foam cell formation. Therefore, a composition containing the ENOblock of the present invention can be very effectively applied to prevent or treat cancer or enolase-associated diseases.

20 Claims, 35 Drawing Sheets

Chemical structures

Microscopic images of ENOblock anti-cancer cell activity

Scale bar=50 μm

Fig. 4b

Mass spectrometry analysis

```
  1 msilkihareifdsrgnptvevdlftskglfraavpsgastgiyealelrdndktrymgk
 61 gvskavehinktiapalvskklnvteqekidklmiemdgtenkskfganailgvslavck
121 agavekgvplyrhiadlagnsevilpvpafnvinggshagnklamqefmilpvgaanfre
181 amrigaevyhnlknvikekygkdatnvgdeggfapnilenkeglellktaigkagytdkv
241 vigmdvaaseffrsgkydldfkspddpsryispdqladlyksfikdypvvsiedpfdqdd
301 wgawqkftasagiqvvgddltvtnpkriakavnekscnclllkvnqigsvteslqackla
361 qangwgvmvshrsgetedtfiadlvvglctgqiktgapcrserlakynqllrieeelgsk
421 akfagrnfrnplak
```

Mascot scores: a=170; b= 155

Fig. 4c

Binding to enolase in cell lysate

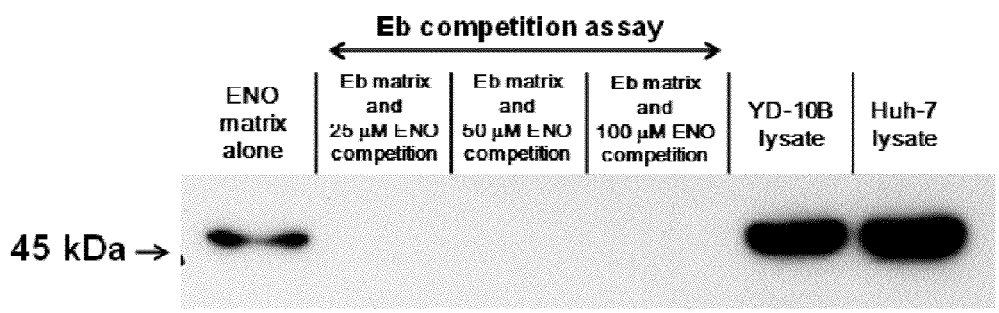

Invasion assay images

Untreated 1.25 μM ENOBlock 2.5 μM ENOBlock

5 μM LY294002

Migration assay images

Untreated

5 µM LY294002

0.625 µM ENOBlock 1.25 µM ENOBlock

Apoptosis-related protein expression

Fig. 9a

Toxicological analysis using zebrafish

| Test Compound | Somite | Tail detachment | Otoliths | Eyes | Heart Beat | Circulation | Delayed Hatching | Skeletal deformities | Lack of swimming |
|---|---|---|---|---|---|---|---|---|---|
| Control | - | - | - | - | - | - | - | - | - |
| ENOblock(10μM) | - | - | - | - | - | - | - | - | - |
| ENOblock(20μM) | - | - | - | - | - | - | - | - | + |
| ENOblock(40μM) | + | - | - | - | - | + | - | + | + |

Schematic for measuring zebrafish PEPCK expression

Zebrafish liver PEPCK expression

Schematic for measuring zebrafish glucose uptake

Glucose uptake in zebrafish

2-NBDG alone

2-NBDG + ENOblock

2-NBDG + emodin

Scale bar=1 mm

Measurement of fluorescence intensity

(i) Visualization of lipid accumulation

Bar=50 μm

(ii) Assay for lipid accumulation

(ii) Foam cell numbers

(iii) Macrophage numbers

PHARMACEUTICAL COMPOSITION FOR PREVENTING OR TREATING CANCER, CONTAINING ENOBLOCK AS ACTIVE INGREDIENT

TECHNICAL FIELD

The present invention was made with the support of the Ministry of Education, Science, and Technology of Republic of Korea, under Project No. NRF-2012-003460, which was conducted under the research project entitled "General Researcher Support Project/Rising Researcher Support Project" within the project named "Discovery and Characterization of Insulinomimetics as Candidate drugs to Treat Diabetes" by the Gwangju Institute of Science and Technology under the management of the National Research Foundation of Korea, from May 1, 2012 to Apr. 30, 2015. Further, the present invention was made with the support of the Ministry of Education, Science, and Technology of Republic of Korea, under Project No. NRF-2012-000462, which was conducted under the research project entitled "General Researcher Support Project/Woman Scientist Support Project" within the project named "Development of Novel Targets and Mechanisms that Modulate Tumor Microenvironment for Anti-Cancer Therapy" by the Gwangju Institute of Science and Technology under the management of the National Research Foundation of Korea, from May 1, 2012 to Apr. 30, 2015. Further, the present invention was made with the support of the Ministry of Health and Welfare of the Republic of Korea, under Project No. A120326, which was conducted under the research project entitled "Health Care Research and Development Project" within the project named "Production of patient autologous iPSCs using low-molecular weight differentiation regulator and application to myocardial infarction cell treatment" by the Gwangju Institute of Science and Technology under the management of the Korea Health Industry Development Institute, from Aug. 1, 2012 to Jul. 31, 2014.

The present patent application claims priority to and the benefit of Korean Patent Application No. 10-2012-0117417 filed in the Korean Intellectual Property Office on Oct. 22, 2012, the disclosures of which are incorporated herein by reference.

The present invention relates to ENOblock, which is a non-substrate analogue having enolase inhibitory activity, and a pharmaceutical composition containing the same for preventing or treating cancer.

BACKGROUND ART

Enolase is a component of the glycolysis pathway and a "moonlighting" protein, with important roles in diverse cellular processes that are not related to its function in glycolysis. However, small molecule tools to probe enolase function have been restricted to crystallography or enzymology. In this study, we report the discovery of the small molecule "ENOblock", which is the first, nonsubstrate analogue that directly binds to enolase and inhibits its activity. ENOblock was isolated by small molecule screening in a cancer cell assay to detect cytotoxic agents that function in hypoxic conditions, which has previously been shown to induce drug resistance. Further analysis revealed that ENOblock can inhibit cancer cell metastasis in vivo. Moreover, an unexpected role for enolase in glucose homeostasis was revealed by in vivo analysis. Thus, ENOblock is the first reported enolase inhibitor that is suitable for biological assays. This new chemical tool may also be suitable for further study as a cancer and diabetes drug candidate.

Glycolysis is an ancient and highly conserved metabolic pathway that converts 1 mol of glucose into 2 mol of pyruvate. Free energy is released and used to form the highenergy-containing compounds adenosine triphosphate (ATP) and reduced nicotinamide adenine dinucleotide (NADH). Glycolysis comprises 10 biochemical reactions, and each step is catalyzed and regulated by a different enzyme. Over the past 20 years, there has been increasing appreciation of the multiple roles glycolytic enzymes play in diverse cellular processes (reviewed in ref 1).

Cancer cells show increased dependence on glycolysis to produce ATP; a phenomenon known as the Warburg effect.[2] This metabolic alteration is a fundamental difference between cancer cells and normal cells, offering a therapeutic strategy to selectively kill cancer cells using glycolysis inhibitors (reviewed in ref 3). It has also been shown that glycolysis inhibitors induce cancer cell death more effectively in a hypoxic environment, which occurs within developing tumors.[4] Moreover, this hypoxic environment renders cancer cells less sensitive to other cancer drugs, such as cytarabine and doxorubicin.[4]

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

DETAILED DESCRIPTION OF THE INVENTION

Technical Problem

The present inventors have endeavored to isolate/identify small molecules that can inhibit cancer cell survival in hypoxic conditions. As a result, the present inventors found that a triazine-based compound named ENOblock directly binds to enolase to inhibit its activity more effectively in hypoxic conditions rather than normoxia conditions; inhibits cancer cell migration, metastasis, and invasion; induces intracellular glucose uptake, down-regulates PEPCK expression, and inhibits adipogenesis and foam cell formation.

Accordingly, an aspect of the present invention is to provide a pharmaceutical composition for preventing or treating cancer.

Another aspect of the present invention is to provide a pharmaceutical composition for preventing or treating enolase-associated disorders.

Another aspect of the present invention is to provide a method for preventing or treating cancer.

Other purposes and advantages of the present disclosure will become clarified by the following detailed description of the invention, claims, and drawings.

Technical Solution

In accordance with an aspect of the present invention, there is provided a pharmaceutical composition for preventing or treating cancer, the composition comprising: (a) a therapeutically effective amount of a triazine-based compound represented by chemical formula I below; and (b) a pharmaceutically acceptable carrier:

Chemical formula I

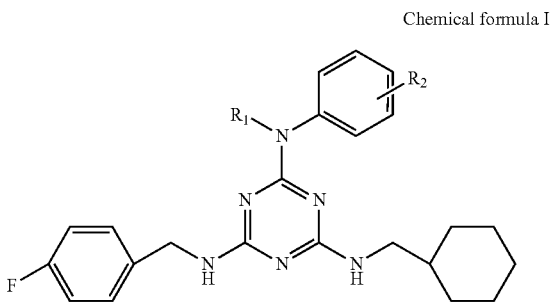

wherein in the chemical formula, $R_1$ is H or $C_1$-$C_5$ straight or branched chain alkyl; $R_2$ is H, $C_1$-$C_5$ straight or branched chain alkyl, $C_1$-$C_5$ straight or branched chain alkyl alcohol, $—[(CH_2)_m—O]_n—(CH_2)_p—NH_2$ (m, n, and p are each an integer of 1 to 10), $—[(CH_2)_m—O]_n—CH_3$ (m and n are each an integer of 1 to 10), $—[(CH_2)_m—O]_n—(CH_2)_p—CH_3$ (m, n, and p are each an integer of 1 to 10), $—(CH_2)_q—(CONH)—C_{1-5}$ straight or branched chain alkyl (q is an integer of 0 to 5), $—(CH_2)_q—(CONH)—C_{1-5}$ straight or branched chain alkyl alcohol (q is an integer of 0 to 5), $—(CH_2)_q—(CONH)—[(CH_2)_m—O]_n—(CH_2)_p—NH_2$ (m, n, and p are each an integer of 1 to 10, and q is an integer of 0 to 5), $—(CH_2)_q—(CONH)—[(CH_2)_m—O]_n—CH_3$ (m and n are each an integer of 1 to 10, and q is an integer of 0 to 5), or $—(CH_2)_q—(CONH)—[(CH_2)_m—O]_n—(CH_2)_p—CH_3$ (m, n, and p are each an integer of 1 to 10, and q is an integer of 0 to 5).

According to another aspect of the present invention, the present invention provides a pharmaceutical composition for preventing or treating enolase-associated disorders, comprising the composition of the above present invention as an active ingredient The present inventors have endeavored to isolate/identify small molecules that can inhibit cancer cell survival in hypoxic conditions. As a result, the present inventors found that a triazine-based compound named ENOblock directly binds to enolase to inhibit its activity more effectively in hypoxic conditions rather than normoxia conditions; inhibits cancer cell migration, metastasis, and invasion; induces intracellular glucose uptake, down-regulates PEPCK expression, and inhibits adipogenesis and foam cell formation.

AP-III-a4 (called "ENOblock"), which is an active ingredient of the present invention, is a triazine-based compound, and is identified from a tagged triazine library of 384 triazine-based compounds using a screening system established by the present inventors, as a small molecule compound that effectively and specifically induces cancer cell death in hypoxic conditions. A synthesis method of the triazine compound library used herein and a use thereof are disclosed in International Patent Publication Nos. WO 03/032903 and WO 03/050237, the disclosures of which are incorporated herein by reference.

In chemical formula I, the term "$C_1$-$C_5$ straight or branched chain alkyl" includes alkyls having straight chain or branched chain such as methylamine, ethylamine, n-propylamine, isopropylamine, n-butylamine, sec-butylamine, tert-butylamine, n-amyl, tert-amyl, and hexyl. Alkyl alcohols include methanol, ethanol, propanol, butanol, benzyl alcohol, penetyl alcohol and their derivates, but not limited thereto.

According to a preferable embodiment of the present invention, in chemical formula I, $R_1$ includes H or $C_1$-$C_2$ alkyl, and more preferably H.

According to a preferable embodiment of the present invention, in chemical formula I, $R_2$ is H, $C_1$-$C_5$ straight or branched chain alkyl, $C_1$-$C_5$ straight or branched chain alkyl alcohol, $—[(CH_2)_m—O]_n—(CH_2)_p—NH_2$ (m, n, and p are each an integer of 1 to 10), $—[(CH_2)_m—O]_n—CH_3$ (m and n are each an integer of 1 to 10), $—[(CH_2)_m—O]_n—(CH_2)_p—CH_3$ (m, n, and p are each an integer of 1 to 10), $—(CH_2)_q—(CONH)—C_{1-5}$ straight or branched chain alkyl (q is an integer of 0 to 5), $—(CH_2)_q—(CONH)—C_{1-5}$ straight or branched chain alkyl alcohol (q is an integer of 0 to 5), $—(CH_2)_q—(CONH)—[(CH_2)_m—O]_n—(CH_2)_p—NH_2$ (m, n, and p are each an integer of 1 to 10, and q is an integer of 0 to 5), $—(CH_2)_q—(CONH)—[(CH_2)_m—O]_n—CH_3$ (m and n are each an integer of 1 to 10, and q is an integer of 0 to 5), or $—(CH_2)_q—(CONH)—[(CH_2)_m—O]_n—(CH_2)_p—CH_3$ (m, n, and p are each an integer of 1 to 10, and q is an integer of 0 to 5).

More preferably, $R_2$ includes H or $C_1$-$C_2$ alkyl, and more preferably H, $C_1$-$C_5$ straight or branched chain alkyl, $C_1$-$C_5$ straight or branched chain alkyl alcohol, $—[(CH_2)_m—O]_n—(CH_2)_p—NH_2$ (m, n, and p are each an integer of 1 to 5), $—[(CH_2)_m—O]_n—CH_3$ (m and n are each an integer of 1 to 5), $—[(CH_2)_m—O]_n—(CH_2)_p—CH_3$ (m, n, and p are each an integer of 1 to 5), $—(CH_2)_q—(CONH)—C_{1-5}$ straight or branched chain alkyl (q is an integer of 0 to 2), $—(CH_2)_q—(CONH)—C_{1-5}$ straight or branched chain alkyl alcohol (q is an integer of 0 to 2), $—(CH_2)_q—(CONH)—[(CH_2)_m—O]_n—(CH_2)_p—NH_2$ (m, n, and p are each an integer of 1 to 5, and q is an integer of 0 to 2), $—(CH_2)_q—(CONH)—[(CH_2)_m—O]_n—CH_3$ (m and n are each an integer of 1 to 5, and q is an integer of to 2), or $—(CH_2)_q—(CONH)—[(CH_2)_m—O]_n—(CH_2)_p—CH_3$ (m, n, and p are each an integer of 1 to 5, and q is an integer of 0 to 2).

According to a preferable embodiment of the present invention, the triazine-based compound represented by chemical formula I above includes a compound represented by chemical formula II below:

Chemical formula II

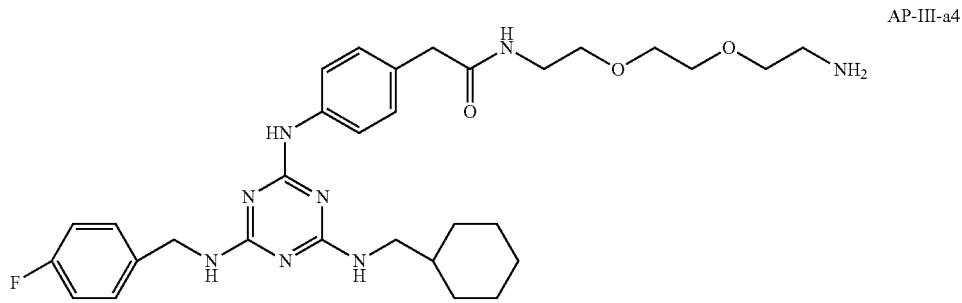

AP-III-a4

The present invention is directed to a first report regarding a small molecule (ENOblock), which is a non-substrate analogue that directly binds to enolase to inhibit its activity.

According to the present invention, ENOblock of the present invention specifically inhibited the activity of enolase in a dose-dependent manner in normoxia conditions or hypoxic conditions, and thus inhibited cancer cell migration, metastasis, and invasion (see FIGS. 1 to 3). The above-described effects were more excellent in hypoxic conditions. Therefore, ENOblock of the present invention can be effectively applied as a cancer or enolase-related disease treatment agent through the inhibition of enolase activity.

According to a preferable embodiment of the present invention, the composition of the present invention inhibits enolase activity, and inhibits cancer cell migration, invasion, and metastasis. According to a preferable embodiment of the present invention, the above-described inhibition effect by ENOblock of the present invention is more promoted in hypoxic conditions rather than normoxia conditions.

According to a preferable embodiment of the present invention, the composition of the present invention reduces the expression of apoptosis-inducible proteins, and more preferably reduces the expression of AKT or Bcl-xL protein.

According to a preferable embodiment of the present invention, the types of cancer that can be prevented or treated by the composition of the invention may include one selected from the group consisting of brain cancer, neuroendocrine cancer, stomach cancer, lung cancer, breast cancer, ovarian cancer, liver cancer, bronchial cancer, nasopharyngeal cancer, laryngeal cancer, pancreatic cancer, bladder cancer, adrenal cancer, large intestine cancer, colon cancer, cervical cancer, prostate cancer, bone cancer, skin cancer, thyroid cancer, parathyroid, and ureter cancer.

Symptoms of the above-described cancers may include breast tubercles, papillary process, breast cystomas, breast pain, death, weight loss, invalidism, excessive fatigue, difficulty in breathing and intake, loss of appetite, chronic sneezing, hemoptysis, hematuria, bloody stools, nausea, vomiting, liver metastases, lung metastases, bone metastasis, colorectal metastasis, bladder metastasis, renal metastasis, pancreatic metastasis, abdominal distension, feeling bloated, intraperitoneal fluid, vaginal bleeding, constipation, bowel perforation, acute peritonitis, pain, excessive sweating, fever, hypertension, anemia, diarrhea, jaundice, dizziness, chills, or muscle cramps.

As used herein, the term "enolase-associated disorders" refers to disorders that are caused by overexpression of enolase, and more preferably means disorders that are caused in hypoxic conditions rather than normoxia conditions, and includes, for example, cancers, autoimmune disorders, and ischemia, but is not limited thereto.

Meanwhile, the composition of the present invention may be also used as a composition for preventing or treating diabetes.

According to a preferable embodiment of the present invention, the composition of the present invention has insulin-mimicking activity.

According to a preferable embodiment of the present invention, the insulin-mimicking activity by the composition of the present invention encompasses the promotion of intercellular glucose uptake.

According to a preferable embodiment of the present invention, the composition of the present invention down-regulates the expression of phosphoenolpyruvate carboxykinase (PEPCK), which is an important protein in gluconeogenesis.

According to a preferable embodiment of the present invention, the composition of the present invention inhibits adipogenesis and foam cell formation.

As used herein, the term "pharmaceutically effective amount" refers to an amount sufficient to attain efficacy or activity (e.g., anti-cancer agent, anti-diabetic agent, etc.) of the above-described triazine-based compound.

The pharmaceutical composition of the present invention includes a pharmaceutically acceptable carrier. The pharmaceutically acceptable carrier contained in the pharmaceutical composition of the present invention is conventionally used for the formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil, but are not limited thereto. The pharmaceutical composition of the present invention may further contain, in addition to the above components, a lubricant, a wetting agent, a sweetening agent, a flavoring agent, an emulsifier, a suspending agent, a preservative, and the like. Suitable pharmaceutically acceptable carriers and agents are described in detail in *Remington's Pharmaceutical Sciences* (19th ed., 1995).

A suitable dose of the pharmaceutical composition of the present invention may vary depending on various factors, such as a method of formulation, manner of administration, the age, body weight, gender, and morbidity of the patient, diet, administration time, excretion rate, and response sensitivity. Meanwhile, the oral dose of the pharmaceutical composition of the present invention is preferably 0.001 to 100 mg/kg (body weight) per day.

The pharmaceutical composition of the present invention may be administered orally or parenterally, and examples of parenteral administration may include intravenous, subcutaneous, intramuscular, intraperitoneal, and transdermal injections. The route of administration of the pharmaceutical composition of the present invention is preferably determined according to the kind of applied disease.

The concentration of the triazine-based compound of chemical formula I, which is an active ingredient contained in the composition of the present invention, may be determined considering the therapeutic purpose, the condition of the patient, the required period, or the like, and is not limited to a specific range of concentration.

The pharmaceutical composition of the present invention is formulated into a unit dosage form or a multidose container, using a pharmaceutically acceptable carrier and/or excipient according to the method that is easily conducted by person having ordinary skills in the art to which the present invention pertains. Here, the dosage form may be a solution in an oily or aqueous medium, a suspension, or an emulsion, or an extract, a powder, a granule, a tablet, or a capsule, and may further include a dispersant or a stabilizer.

According to another aspect of the present invention, the present invention provides a method for preventing or treating cancer, the method comprising administering to a subject a composition containing: (a) a therapeutically effective amount of a triazine-based compound represented by chemical formula I below; and (b) a pharmaceutically acceptable carrier:

Chemical formula I

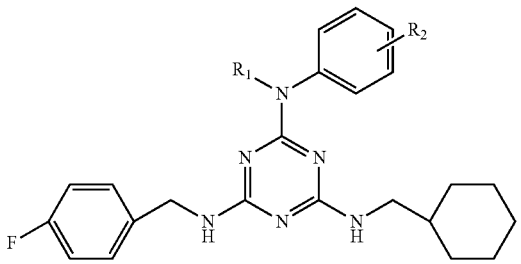

wherein in the chemical formula, $R_1$ is H or $C_1$-$C_5$ straight or branched chain alkyl; $R_2$ is H, $C_1$-$C_5$ straight or branched chain alkyl, $C_1$-$C_5$ straight or branched chain alkyl alcohol, —[$(CH_2)_m$—O]$_n$—$(CH_2)_p$—$NH_2$ (m, n, and p are each an integer of 1 to 10), —[$(CH_2)_m$—O]$_n$—$CH_3$ (m and n are each an integer of 1 to 10), —[$(CH_2)_m$—O]$_n$—$(CH_2)_p$—$CH_2$ (m, n, and p are each an integer of 1 to 10), —$(CH_2)_q$—(CONH)—$C_{1-5}$ straight or branched chain alkyl (q is an integer of 0 to 5), —$(CH_2)_q$—(CONH)—$C_{1-5}$ straight or branched chain alkyl alcohol (q is an integer of 0 to 5), —$(CH_2)_q$—(CONH)—[$(CH_2)_m$—O]$_n$—$(CH_2)_p$—$NH_2$ (m, n, and p are each an integer of 1 to 10, and q is an integer of 0 to 5), —$(CH_2)_q$—(CONH)—[$(CH_2)_m$—O]$_n$—$CH_3$ (m and n are each an integer of 1 to 10, and q is an integer of 0 to 5), or —$(CH_2)_q$—(CONH)—[$(CH_2)_m$—O]$_n$—$(CH_2)_p$—$CH_3$ (m, n, and p are each an integer of 1 to 10, and q is an integer of 0 to 5).

Since the method of the present invention uses the above-described composition, descriptions of overlapping contents between the two are omitted to avoid excessive complication of the specification due to repetitive descriptions thereof.

Advantageous Effects

Features and advantages of the present invention are summarized as follows:

(a) The present invention relates to ENOblock, which is a non-substrate analogue having an enolase inhibitory activity, and a pharmaceutical composition for preventing or treating cancer or enolase-associated diseases, containing the same.

(b) The ENOblock of the present invention directly binds to enolase so as to inhibit an activity thereof, and the inhibition is more effective in hypoxia than in normoxia.

(c) In addition, the ENOblock of the present invention inhibits migration, metastasis and invasion of cancer cells.

(d) Furthermore, the ENOblock of the present invention induces glucose uptake into cells, down-regulates the expression of PEPCK, and inhibits adipogenesis and foam cell formation.

(f) Therefore, a composition containing the ENOblock of the present invention can be very effectively applied to prevent or treat cancer or enolase-associated diseases.

Fluoride 2 mM=0.000376; EnoBlock 2.5 µM=0.000527; EnoBlock 5 µM=0.000474; EnoBlock 10 µM=0.000335.

Figure 5:
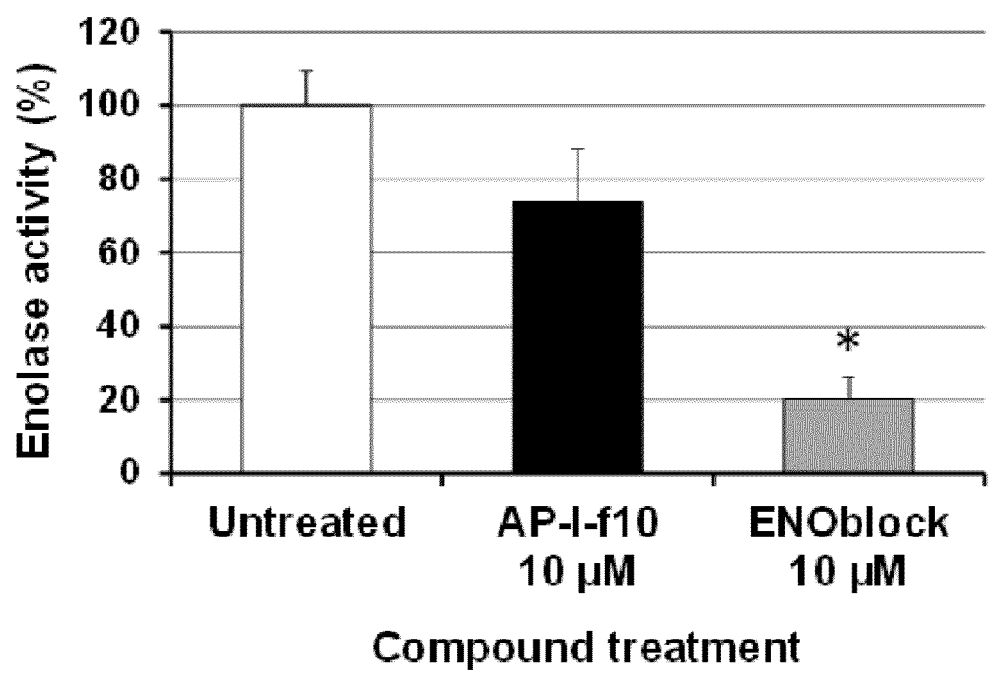

FIG. 5. AP-I-f10, a "non-hit" compound from the same triazine library as ENOblock, did not significantly inhibit enolase activity. ENOblock was used as a positive control. Error=SD; *=P<0.05 compared to the untreated group.

Figure 6:
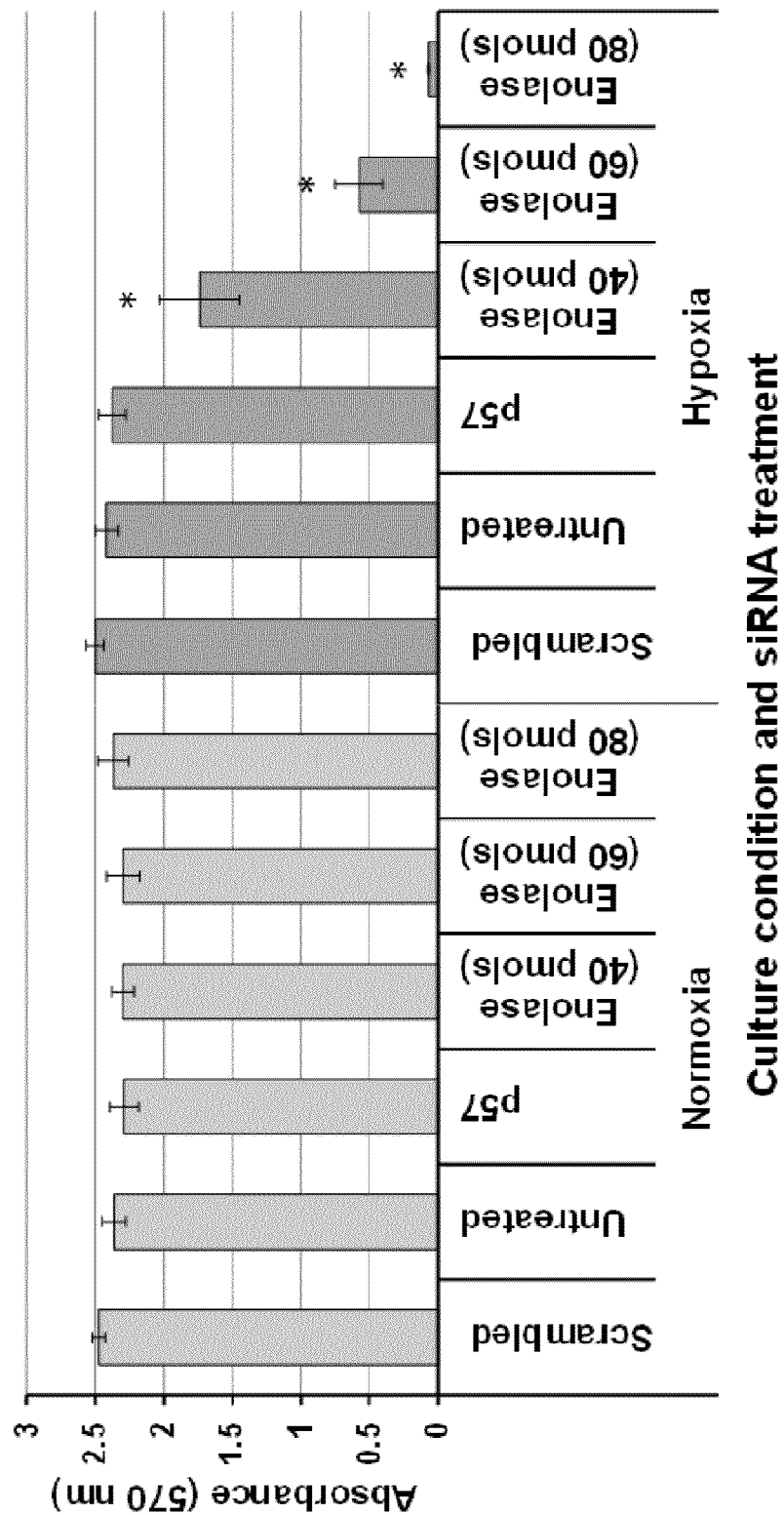

FIG. 6. SiRNA-mediated known of enolase expression in HCT116 cancer cells increased susceptibility to hypoxia. Cells were treated with increasing concentrations of enolase (ENO1) siRNA or two types of negative control siRNA: 1) 80 pmols scrambled or 2) 80 pmols p57 (a cyclin dependent kinase inhibitor). 24 h post-transfection with siRNA, cells were transferred to a 96-well culture plate at a density of $10^4$ cells/well and, 24 h later, cultured in normoxia or exposed to hypoxia by treatment with 150 mM $CoCl_2$. Cytotoxicity was assessed by MTT assay 24 h later. Increasing concentrations of ENO1 cytotoxicity under hypoxia compared to normoxia. Error=SD; *=P<0.05 compared to normoxia. P value: enolase in hypoxia (40 pmols)=0.00990; enolase in hypoxia (60 pmols)=$3.32 \times 10^{-6}$; enolase in hypoxia (80 pmols)=$1.43 \times 10^{-8}$.

FIG. 7. ENOblock can inhibit cancer cell invasion and migration. (a) ENOblock treatment of HCT116 cancer cells under normoxia inhibited invasion dose-dependently. ENOblock significantly inhibits cancer cell invasion at a treatment concentration of 0.625 µM (P value=0.0481), whereas treatment with 5 µM LY294002 reduced cancer cell invasion, but without achieving statistical significance (P value=0.27). Error=SD; *=P<0.05 compared to the untreated group. P value: EnoBlock 2.5 µM=0.0191; EnoBlock 1.25 µM=0.0286; EnoBlock 0.625 µM=0.0481. (b) Microscopic images of crystal violet stained HCT116 cells invaded onto the transwell inserts (scale bar=100 µm). (c) ENOblock treatment of HCT116 cancer cells under normoxia inhibited cell migration dose-dependently. Similar to cell invasion, ENOblock was more effective than LY294002 at inhibiting cell migration. Error=SD; *=P<0.05 compared to the untreated group. P value: EnoBlock 2.5 µM=0.00939. (d) Microscopic images of crystal violet stained HCT116 cells migrated onto the transwell inserts (scale bar=100 µm). (e) ENOblock treatment of HCT116 cancer cells increased sensitivity to the antitubulin chemotherapeutics taxol and vincristine. Cells were treated with 10 nM taxol and 10 nM vincristine, with or without 10 µM ENOblock. Error=SD; *=P<0.05 between the groups indicated on the graph. P value: taxol compared to ENOblock+taxol=$2.55 \times 10^{-6}$; vincristine compared to EnoBlock+vincristine=0.000304. (f) ENOblock treatment of HCT116 cancer cells decreased the expression of AKT and Bcl-Xl, which are negative regulators of apoptosis. For the AKT Western blot, cells were treated with ENOblock for 24 h; for the Bcl-Xl Western blot, cells were treated with ENOblock for 48 h.

Figure 8:
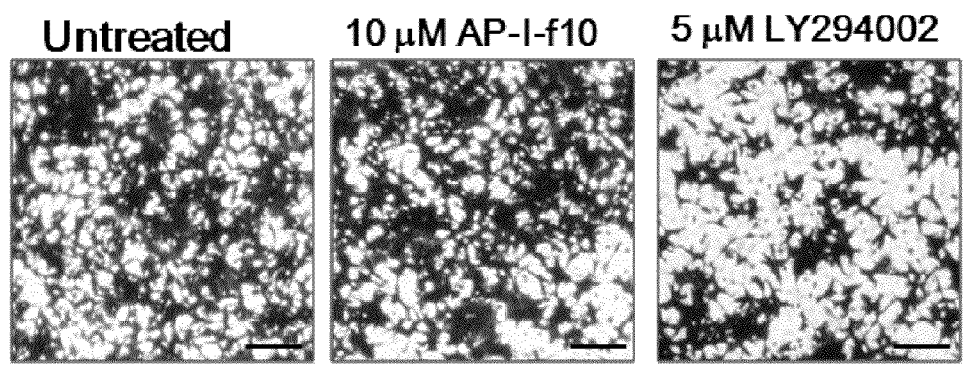

FIG. 8. Micrographs of crystal violet stained transwell insert show that treatment with 10 µM compound AP-I-f10 does not reduce HCT116 colon cancer cell invasion. Treatment with 5 mM LY294002 was used as a positive control and produced a noticeable reduction in invaded cancer cells.

FIG. 9. Toxicological study of ENOblock and in vivo analysis of anticancer activity. (A) Toxicological analysis of ENOblock treatment using the zebrafish larvae system. Assessment of various developmental parameters showed that a dose of 10 µM ENOblock could be tolerated by the larvae, but a dose of 20 µM ENOblock inhibited the ability to swim. (B) Microscopic assessment of 72 days post fertilization (dfp) zebrafish larvae exposed to increasing doses of ENOblock. It can be seen that a dose of 20 µM ENOblock produced an abnormally large swim bladder, as indicated by the red arrow. A dose of 40 µM ENOblock produced multiple abnormalities in the larvae. (C) Doses of 20 or 40 µM ENOblock also reduced overall zebrafish larvae viability, while a dose of 10 µM ENOblock did not affect viability. Error=SD; *=P<0.05 compared to the DMSO treated group. P value: 20 µM ENOblock=0.0121; 40 µM ENOblock=0.0019. (D) Treatment of HCT116-xenotransplanted zebrafish with a dose of 10 µM ENOblock for 96 h reduced the number of embryos showing migration and metastasis (distributed cancer cells) from the yolk sac injection site. DMSO treatment served as a control. Three representative embryos are shown from each experimental group, and distributed cancer cell foci are designated with blue arrows. Quantification of xenotransplanted cancer cell microfoci confirmed that ENOblock treatment significantly reduced cancer cell migration and metastasis. Error=SD; *=P<0.05 compared to the DMSO-treated group.

FIG. 10. ENOblock can induce glucose uptake and inhibit phosphoenolpyruvate carboxykinase (PEPCK) expression. (a) Ten micromolar ENOblock (abbreviated as ENO) treatment of Huh7 hepatocytes or HEK kidney cells for 24 h induced glucose uptake, as measured using the fluorescent glucose probe, 2-NBDG. Twenty-four hour treatment with 10 µM GAPDS, a small molecule modulator of the glycolytic enzyme GAPDH, could also induce glucose uptake in the hepatocytes. In contrast, 24 h treatment with 10 µM rosiglitazone (abbreviated as ROSI), a wellknown anti-diabetes drug, could induce glucose uptake in hepatocytes, but not kidney cells. Error=SD; *=P<0.05 compared to the untreated group. P value (hepatocyte): ROSI=0.0227; GAPDS=0.0302; ENO=0.0213; P value (kidney cell): GAPDS=0.0231; ENO=0.0271. (b) Ten micromolar ENOblock treatment of Huh7 hepatocytes for 24 h inhibited expression of PEPCK, a key positive regulator of gluconeogenesis. Twenty-four hour treatment with 10 µM rosiglitazone could also inhibit PEPCK expression. However, 24 h treatment with 10 µM GAPDS did not inhibit PEPCK expression. Error=SD; *=P<0.05 compared to the no drug (DMSO-treated) group. P value: GAPDS=0.00213; ENO=0.00466. (c) Ten micromolar ENOblock treatment of HEK cells for 24 h inhibited expression of PEPCK. In contrast, treatment with 10 µM GAPDS, 1 µg/mL insulin (abbreviated as Ins), or 10 µM rosiglitazone for 24 h did not reduce PEPCK expression. Error=SD; *=P<0.05 for reduced PEPCK expression compared to the no drug (DMSO-treated) group. P value: ENO=0.000393. (d) Ten micromolar ENOblock treatment of hepatocytes for 24 h did not affect expression of the enzymes glucose 6-phosphatase (G6 Pase), which also regulates gluconeogenesis, or 5' AMP-activated protein kinase (AMPK), which regulates cellular energy homeostasis. Similarly, 24 h treatment with either 10 µM GAPDS or 10 µM rosiglitazone for 24 h did not affect the expression of these enzymes (Error bar=SD).

Figure 11:
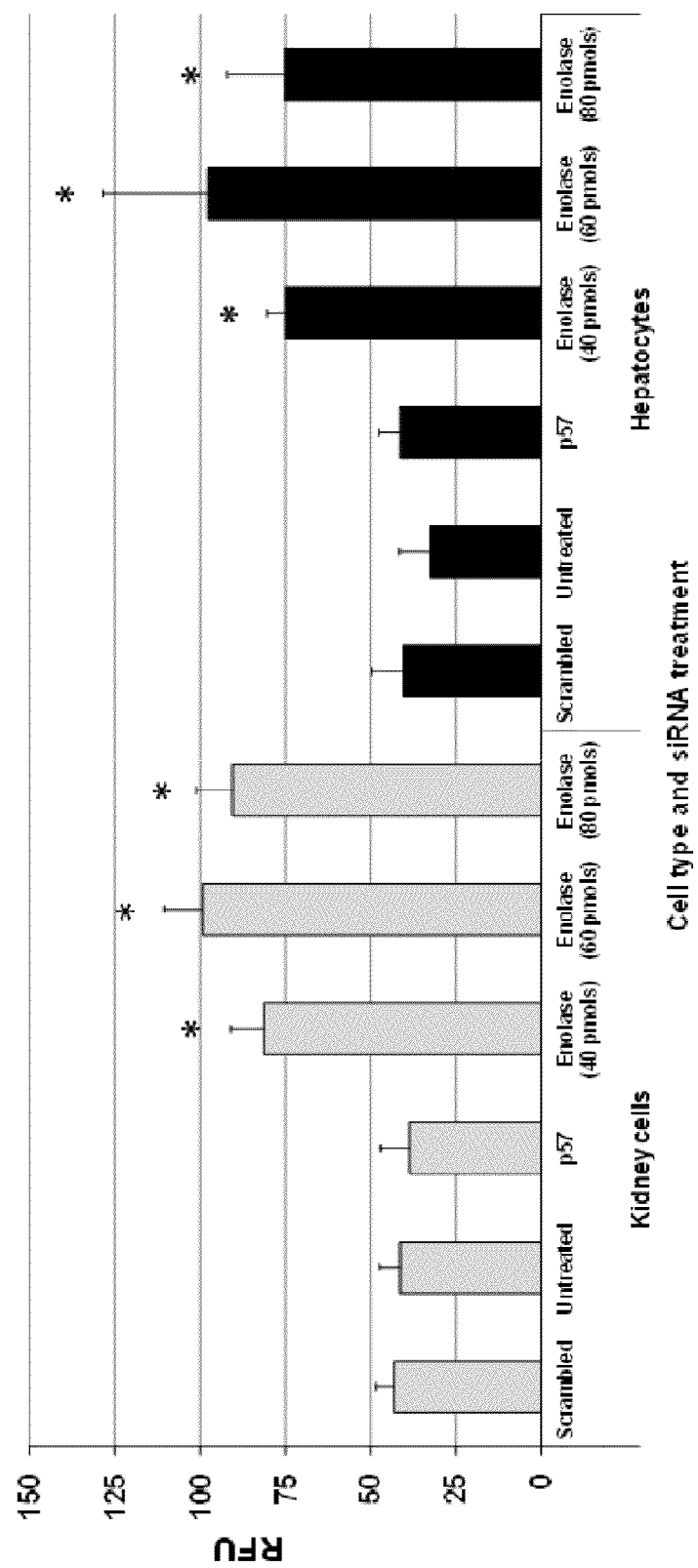

FIG. 11. siRNA-mediated knockdown of enolase expression in hepatocytes or kidney cells induced glucose uptake, as shown by increased labeling with the fluorescent glucose probe, 2-NBDG. Cells were treated with increasing concentrations of enolase (ENO1) siRNA or two types of negative control siRNA: (a) 80 pmols scrambled or (b) 80 pmols p57 (a cyclin dependent kinase inhibitor). Twenty-four hours post-transfection with siRNA, cells transferred to a 96-well culture plate at a density of $10^4$ cells/well and, 24 h later, treated with 100 µM 2-NBDG for 30 min. 2-NBDG fluorescence was then measured as described in Methods. Error=SD; *=P<0.05 for increased glucose uptake compared to cells treated with scrambled siRNA. P value: (a) kidney cells, i) enolase (40 pmols)=$1.83 \times 10^{-5}$, ii) enolase (60 pmols)=$1.76 \times 10^{-6}$, iii)

enolase (80 pmols)=5.1×10⁻⁶; (b) hepatocyte, i) enolase (40 pmols)=2.42×10⁻⁵, ii) enolase (60 pmols)=0.00264, iii) enolase (80 pmols)=0.00239.

FIG. 12. ENOblock can inhibit PEPCK expression and induce glucose uptake in vivo. (a) Schematic of our approach to measure the effect of ENOblock treatment on PEPCK in zebrafish. (b) Three hour treatment with a dose of 10 μM ENOblock inhibited PEPCK expression in adult zebrafish liver. Three hour treatment with 10 μM rosiglitazone, which inhibited PEPCK expression in hepatocytes, also inhibited PEPCK expression in the zebrafish liver. Error=SD; *=P<0.05 compared to the untreated group. P value: ROSI=0.00310; ENO=5.02×10⁻⁵. (c) Schematic of our approach to measure uptake of a fluorescenttagged glucose bioprobe (2-NBDG) in zebrafish larvae, which can be imaged due to their transparency. (d) Four hours treatment with a dose of 10 μM ENOblock increased glucose uptake in the zebrafish larvae. Increased glucose uptake can be observed throughout the developing embryo and, especially, in the eye (indicated by the white arrow), intestine, and yolk sac. As a comparison, zebrafish treated with 10 μg/mL emodin, a known anti-diabetic natural product that promotes glucose uptake, also showed enhanced glucose uptake in a similar but more intense pattern compared to the zebrafish treated with ENOblock. (e) Quantification of fluorescence signal intensity from the fluorescent glucose probe 2-NBDG in the eye of the 72 hpf zebrafish larvae, which is known to express numerous glucose transporters at this stage of development. Four hour treatment of the larvae with a dose of 10 μM ENO block or 10 μg/mL emodin induced significantly greater fluorescent tagged glucose uptake in the zebrafish eye. Error=SD; *=P<0.05 compared to the zebrafish treated with 2-NBDG alone. P value: NBDG+ENOblock=0.0252; NBDG+Emodin=0.0203.

Figure 13:
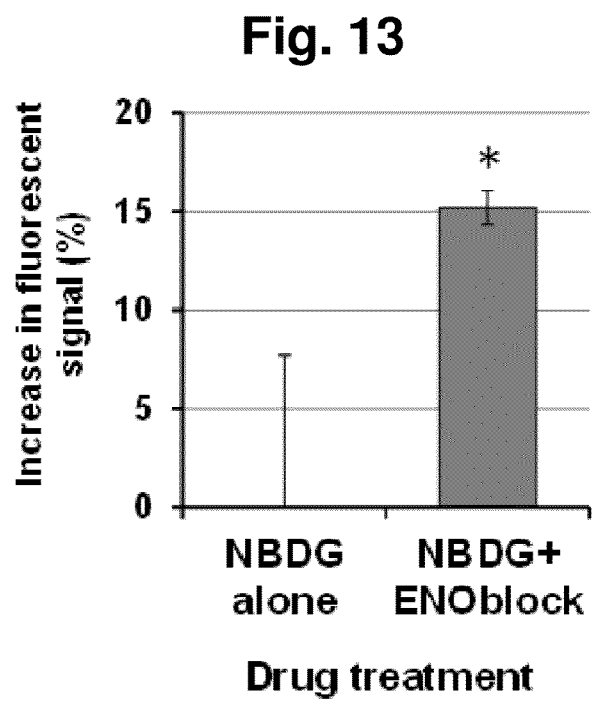

FIG. 13. Treatment of 72 hpf zebrafish with 10 mM ENOblock for 1 h induced glucose uptake, as assessed by fluorescent plate reader measurement of the 2-NBDG signal in lysed larvae (Error=SD; *=P<0.05).

FIG. 14. ENOblock inhibits adipogenesis and foam cell formation. (a) (i) Microscopic analysis of pre-adipocytes undergoing adipogenesis showed that treatment with 10 μM ENOblock inhibited lipid accumulation, as shown by an absence of Oil Red 0 staining. In contrast, treatment of preadipocytes with insulin, without adipogenesis-inducing factors, still induced lipid accumulation. (a) (ii) Quantification of lipid accumulation confirmed that ENOblock treatment blocked lipid accumulation during adipogenesis. Error=SD; *=P<0.05 compared to untreated adipocytes. P value: insulin only=0.004793; adipogenic cocktail only=0.0252. (b) Microscopic analysis of macrophages treated with oleic acid showed that treatment with 10 μM ENOblock inhibited foam cell formation, as shown by reduced Oil Red 0 staining. (c) Confirmation that 10 μM ENOblock inhibited foam cell formation, as assessed by counting cells that showed lipid accumulation. In contrast, macrophage treatment with the anti-diabetes drug rosiglitazone (10 μM) during development into foam cells did not affect the number of cells showing lipid accumulation. Error=SD; *=P<0.05 for reduced lipid-containing cells compared to the oleic acid treated group adipocytes. P value: oleic acid+ENOblock=0.0335. (d) Treatment of monocytes with 10 μM ENOblock inhibited differentiation into macrophages, as assessed by counting the number of cells attached to the culture dish. In contrast, monocyte treatment with 10 μM rosiglitazone did not affect differentiation into macrophages. Error=SD; *=P<0.05 for reduced numbers of attached cells compared to the phorbol 12-myristate 13-acetate (PMA) treated group. P value: PMA+ENOblock=0.0235. (e) The effects of ENOblock treatment on macrophages was not due to cytotoxicity, as shown by MTT assay analysis. Treatment with 3 mM H2O2 for 48 h was used as a positive control. Error=SD; *=P<0.05 for reduced absorbance (570 nm) compared to the untreated group. P value: 3 mM $H_2O_2$=8.84×10⁻⁷.

Figure 15:
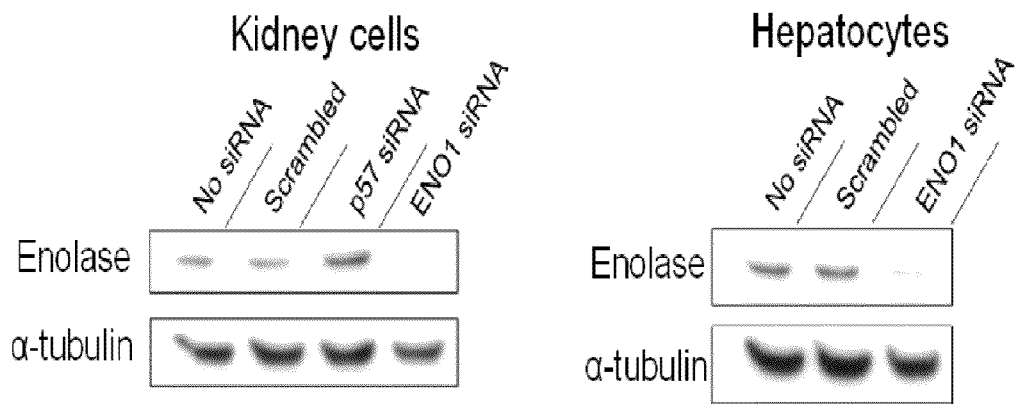

FIG. 15. Immunoblot analysis to confirm enolase expression knockdown via siRNA treatment in HEK kidney cells and Huh7 hepatocytes cells were transfected with 80 pmols siRNA for 48 h.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

Examples

Methods

Construction of the Tagged Triazine Library

The tagged triazine library was prepared according to the procedure reported previously (FIG. 1; 5). The purity of synthesized compounds was determined by analytical HPLC (Agilent Technologies, Santa Clara, USA).

Screening for Apoptosis Inducers that Maintain Effectiveness Under Hypoxia

HCT116 colon carcinoma cells were seeded in 2 sets of 96 well plates at a density of 5×10³ cells per well. 'Low glucose' DMEM (containing 5 mM glucose; Invitrogen, OR, USA) was used for screening, because glycolysis inhibitors, such as 2-Deoxy-D-glucose (2-DG), are effective by competing with glucose. 24 h later, the hypoxic condition was induced in one set of 96 well plates by treatment with 150 μM of 0.22 μm filtered $CoCl_2$ and the culture media volume was reduced by 50% (to 100 μL/well), as previously described.⁴⁹ 4 h later, test compounds from a tagged triazine library⁵ were screened at a concentration of 5 μM in duplicate wells. Cytotoxicity was determined by MTT assay 24 h after adding drug. 'Hits' for further analysis were classified as compounds that 25% or higher cytotoxicity in the hypoxia condition compared to the normoxia condition (as measured by MTT assay absorbance). 50 μM 2-DG, an inhibitor of glycolysis that selectively kills cancer cells in hypoxic conditions⁵⁰, was used as a positive control.

Figure 1A:
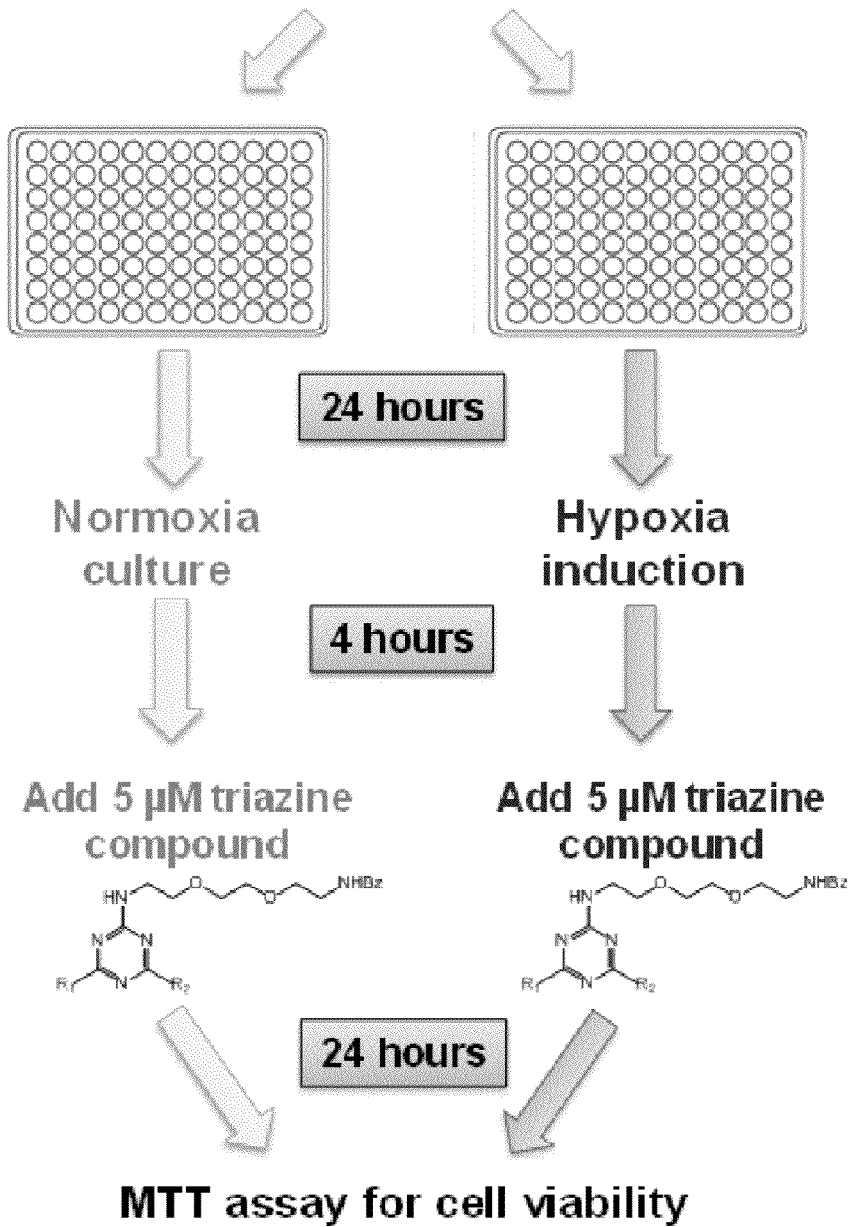
FIG. 1. Discovery of compound AP-III-a4 (ENOblock). (a) Schematic of the screening system used to detect apoptosis inducers effective under hypoxia. HCT116 cancer cells were seeded in parallel 96-well culture plates. Hypoxia was induced in one plate using 150 µM cobalt chloride treatment. Triazine library compound at 5 µM concentration was added 4 h later, and cell death was determined 24 h after hypoxia induction. "Hit" compounds induced 25% or greater levels of cell death under hypoxia compared to normoxia (as measured by MTT assay absorbance). (b) Chemical structures of AP-III-a4 (ENOblock) and the control compounds, AP-IV-e3 and AP-I-f10. Chemical structures of GAPDS, which targets glyceraldehyde 3-phosphate dehydrogenase (GAPDH), and rosiglitazone, a well-known anti-diabetes drug, are also shown. (c) ENOblock induced higher levels of HCT116 colon cancer cell death in hypoxic conditions (Hypox) compared to normoxia (Norm). Error=SD; *=P value<0.05 for increased cell death compared to normoxia. P value: hypox 10=1.23× $10^{-6}$; hypox 5=2.38×$10^{-6}$; hypox 2.5=1.16×$10^{-5}$; hypox 1.25=0.000334. (d) Representative phase contrast microscopic images of HCT116 colon cancer cells treated with ENOblock under normoxia or hypoxia.
Figure 1B:
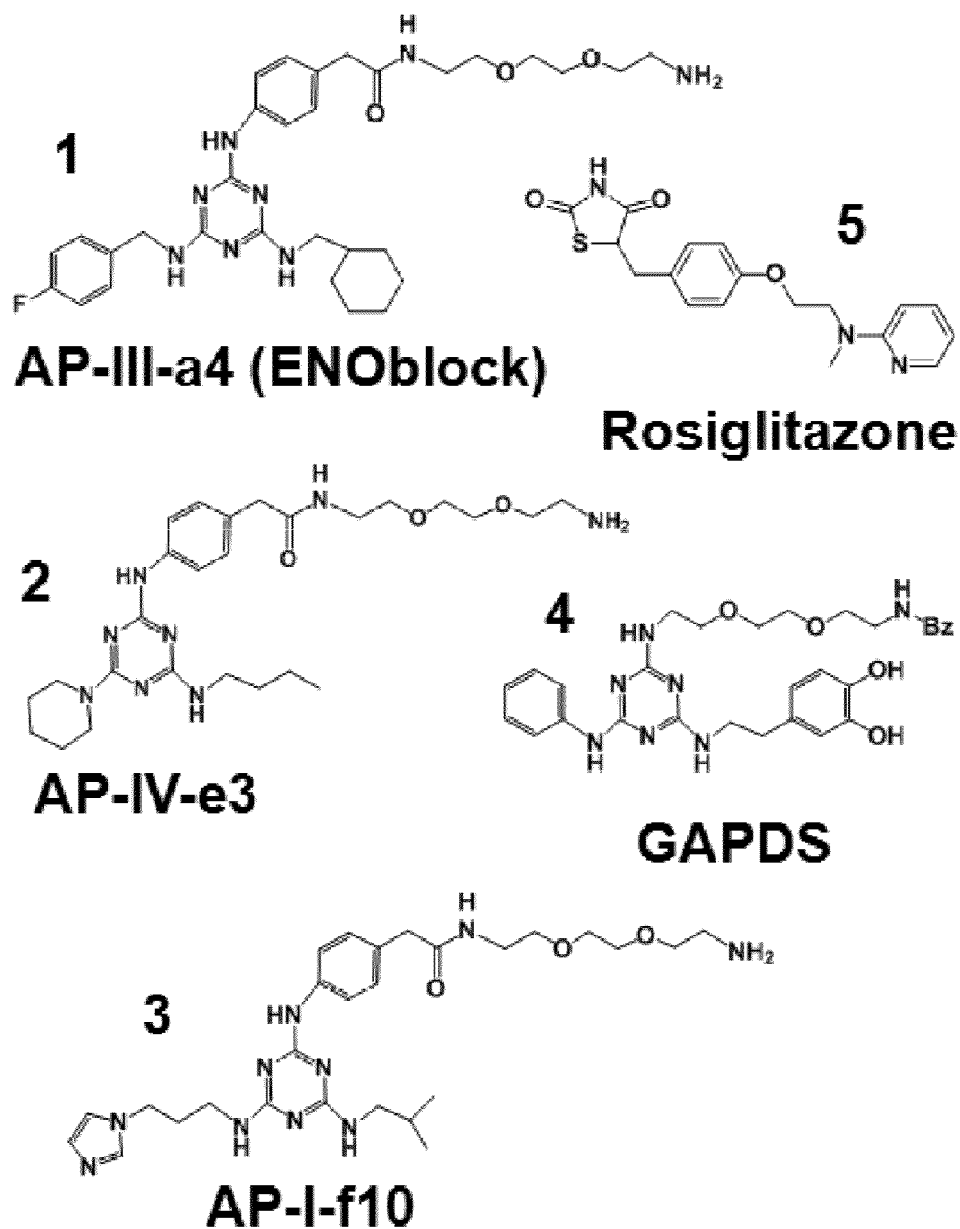
Figure 1C:
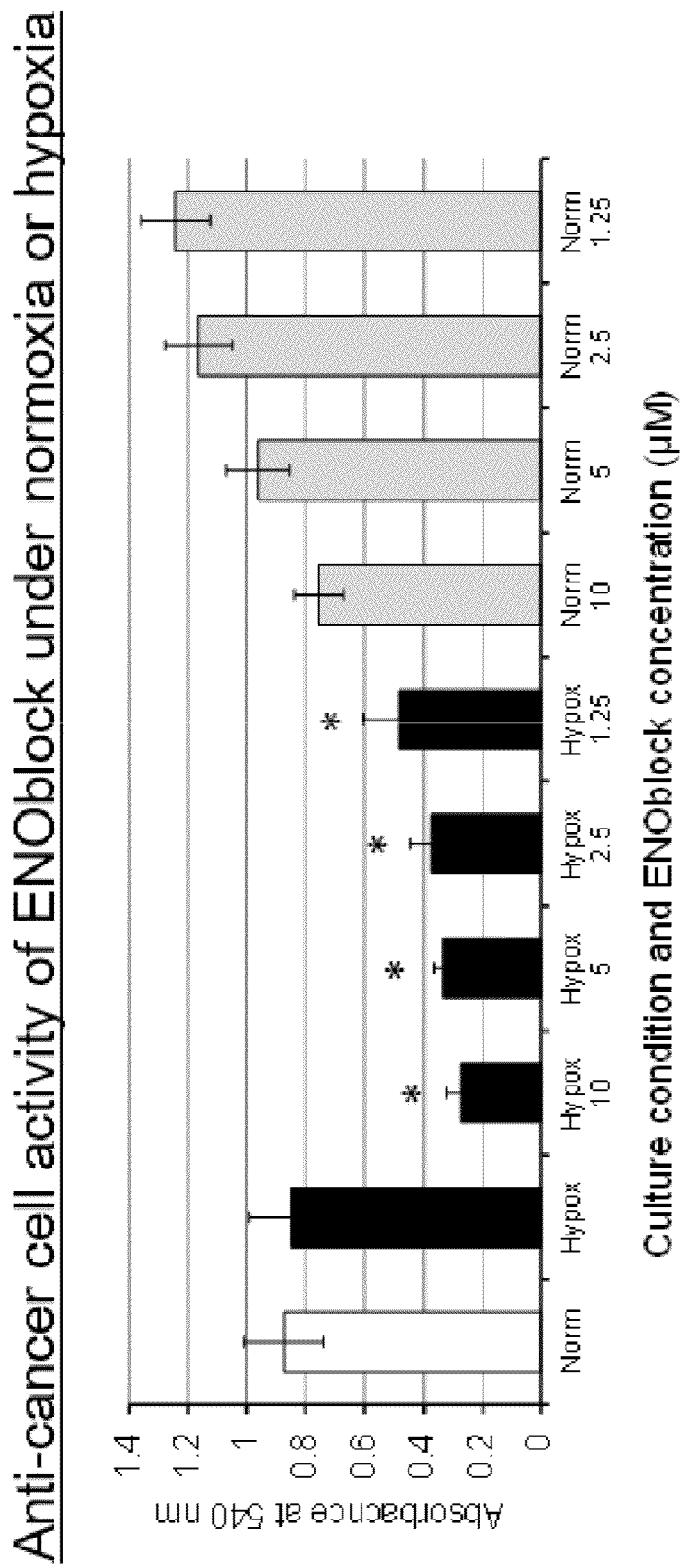
Figure 1D:
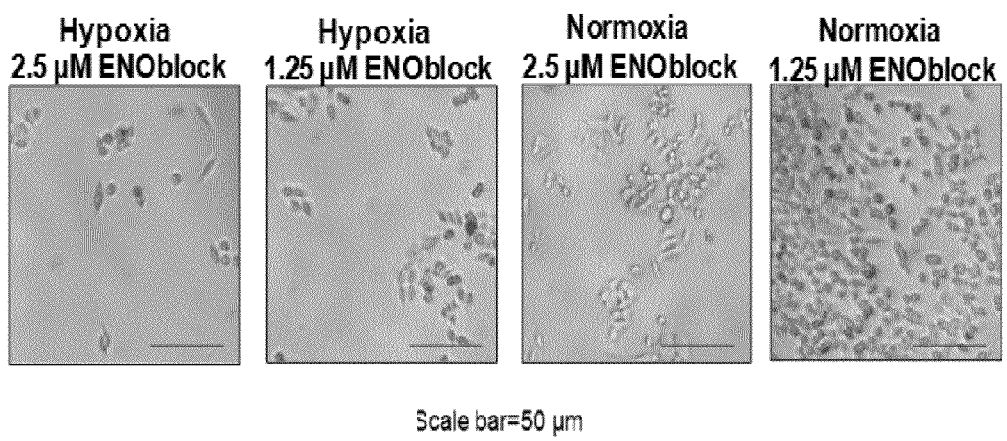
Figure 2:
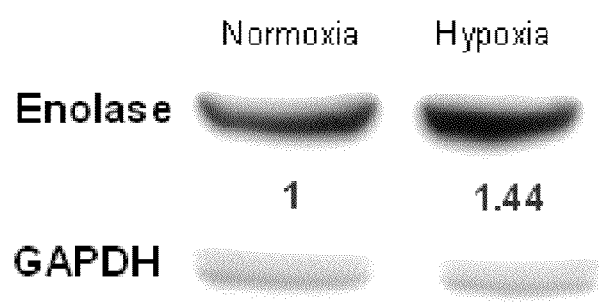
FIG. 2. Treatment of HCT115 cancer cells with 150 µM $CoCl_2$ for 4 h produced a hypoxic environment, as shown by increased expression of the hypoxia-responsive gene, enolase. In contrast, a different protein from the glycolysis pathway, glyceraldehyde 3-phosphate dehydrogenase (GAPDH) did not show increased expression after inducing hypoxia, which is consistent with previous report (Said, et al, BMC Mol Biol. 8: 55 (2007). Red numbers are densitometry analysis to calculate the fold-change in expression.
Figure 3A:
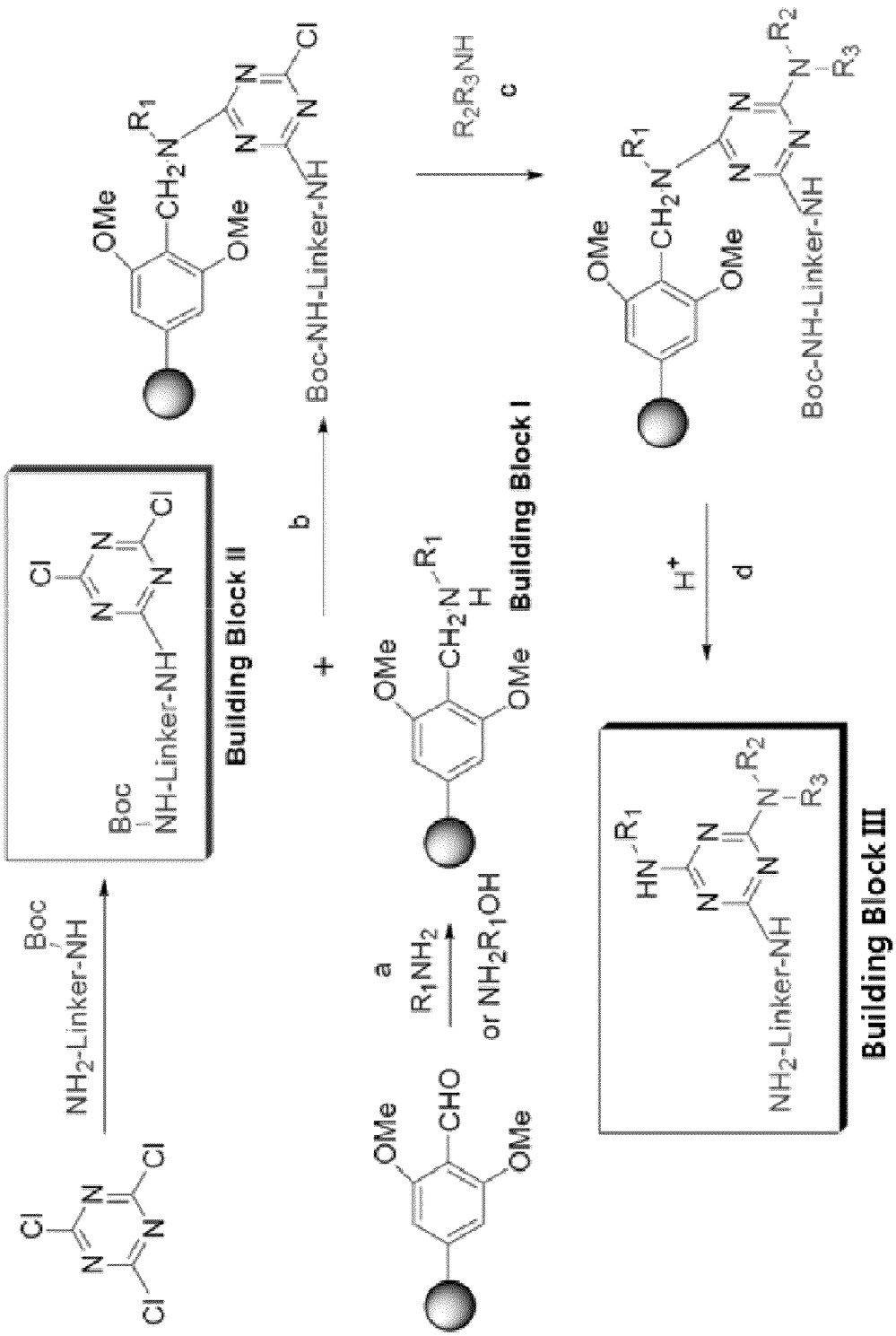
FIG. 3. Synthesis of the linker library. 3a) General scheme for orthogonal synthesis reagents and conditions: (a) $R_1NH_2$ or $R_1NH_2OH$ (5 eq), 2% acetic acid in THF, rt, 1 hr, followed by $NaB(OAc)_3H$ (7 eq), rt, 12 hr; (b) Building block 11 (4 eq) in THF 60° C., 1 hr, DIEA (n,n-diisopropylethylamine); (c) $R_2R_3'NH$, DIEA, NMP:n-BuOH=1:1, 120° C., 3 hr; and (d) 10% TFA (trifluoroacetic acid) in dichloromethane, 30 min. 3b) Linker. 3c) Amines and amino alcohols used for construction of building block I and 3d) Amines used for construction of building block III.
Figure 3B:
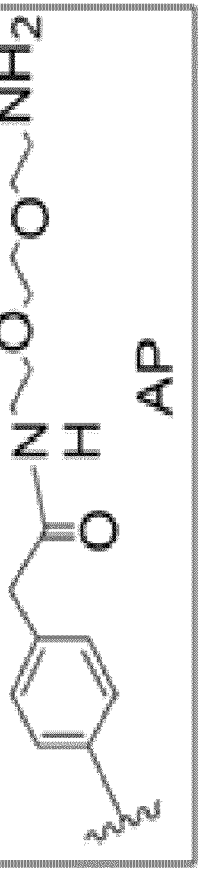
Figure 3C:
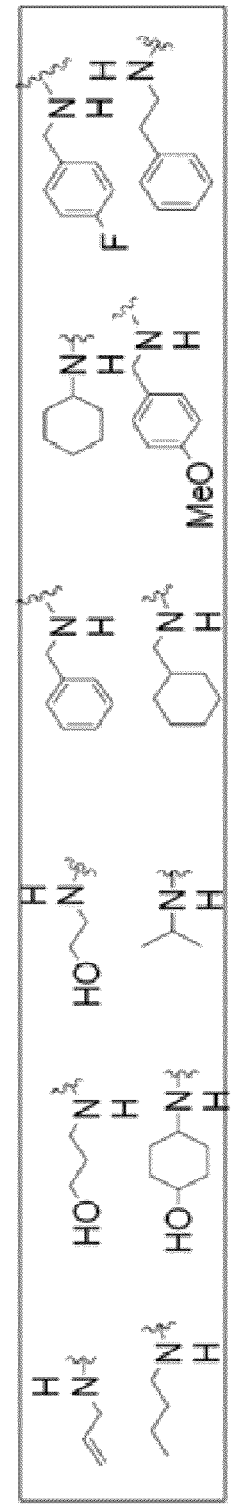
Figure 3D:
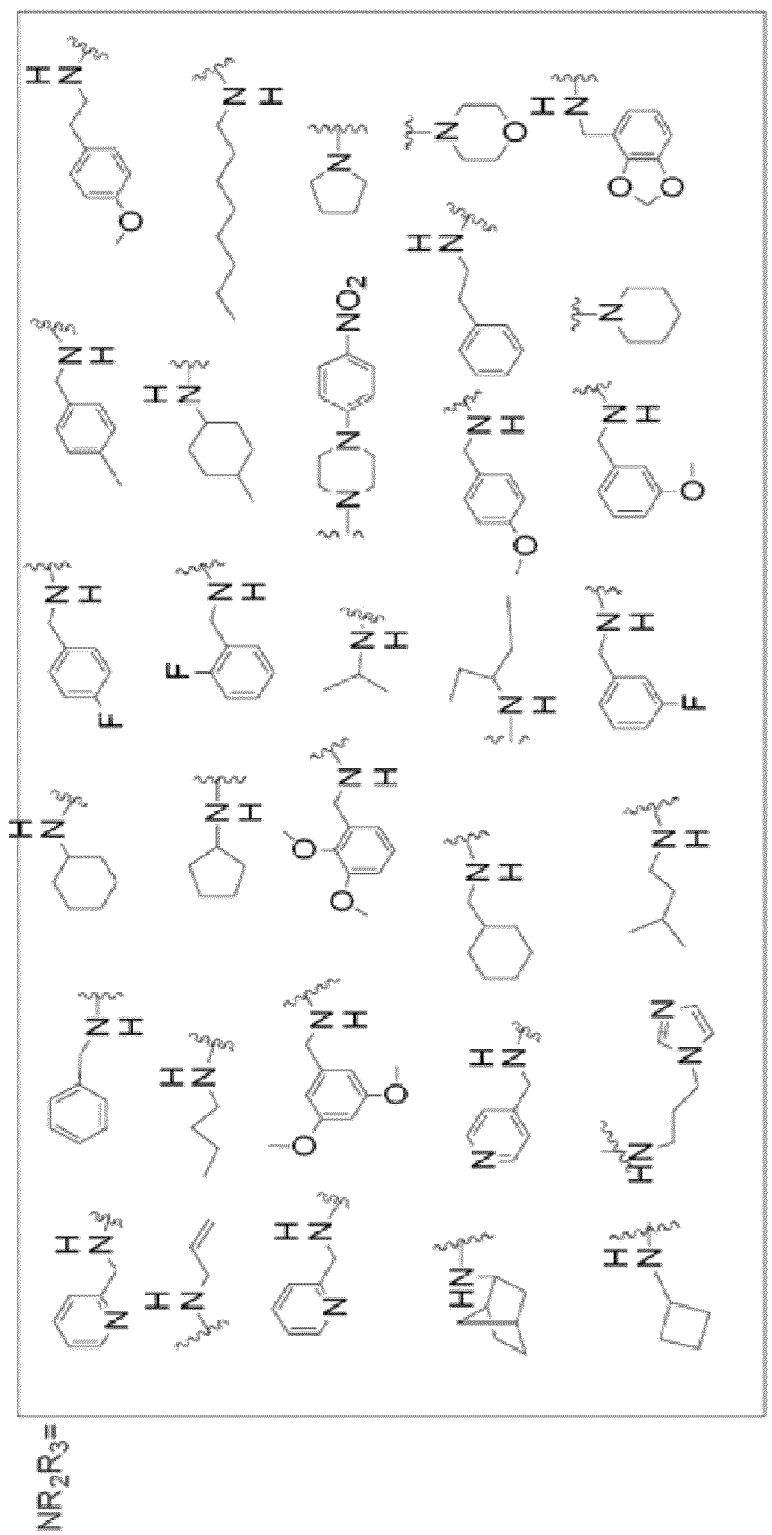

To confirm that $CoCl_2$ treatment induced hypoxia, enolase expression was measured. Enolase expression is known to increase in response to hypoxia.⁵¹ Treatment of HCT116 carcinoma cells with 150 μM $CoCl_2$ for 4 h induced enolase expression (FIG. 2).

Enolase Activity Assay

Enolase purified from rabbit muscle was purchased from Sigma-Aldrich. A single unit of enolase is defined as the amount of enzyme that produces 1 μmol of phosphoenol pyruvate from phospho-D-glycerate/min in standard assay.⁵² Enolase activity assay was measured at 37° C. by incubating pure enolase (3-9 U) in a buffer containing 50 mM imidazole-HCl (pH 6.8)(JUNSEI), 2.0 mM $MgSO_4$ (JUNSEI) and 400 mM KCl (JUNSEI) in the absence or presence of ENOblock or NaF (Sigma). The reaction was initiated by adding 1 μmol of 2-phospho-D-glycerate, and the OD was measured after 10 min of reaction time with a spectrophotometer at 240 nm.

Zebrafish Tumor Cell Xenograft Model

Zebrafish embryos were obtained using standard mating conditions[53] and staged for cell xenoplantation at 48 h post fertilization. After staining of cancer cells (described below), embryos were de-chorionized using micro-forceps and anesthetized with 0.0016% tricaine and positioned on their right side on a wet 1.0% agarose pad. Tumor cells were detached from culture dishes using 0.05% trypsin-EDTA and washed twice with PBS at room temperature. Cells were stained with 2 µg/ml DiI diluted in PBS and washed four times: once with FBS, twice with PBS and then once with 10% FBS diluted in PBS. Cells were kept on ice before injection. Cancer cells were counted by microscopy, suspended in 10% FBS and 100 cells were injected into the center of the yolk sac using an injector equipped with borosilicate glass capillaries (PV820 pneumatic picopump, World Precision Instruments). Injected embryos were transferred to a 96-well plate (one embryo/well) containing drug of interest diluted in 200 mL E3 media (without methylene blue) and maintained at the pre-selected incubation temperature. At 4 days post injection, the number of embryos exhibiting cancer cell dissemination from the injection site was counted and photographed using upright microscopy (Leica DM2500 microscope, Germany). The number of migrated cells was counted and embryos that exhibited more than 5 fluorescent microfoci distant from the yolk sac were scored for cell dissemination.

Measurement of Glucose Uptake in Zebrafish

At 72 hpf, larvae were placed into a 96-well plate (6 eggs/well in 200 µL E3 water supplemented with 0.2 mM 2-phenylthiourea; Sigma). Drug of interest was added for h. The solution was then replaced with E3 water supplemented with 600 µM 2-NBDG and incubated for 3 h. The larva were washed with E3 water and anesthetized with 0.02% tricaine-supplemented E3 water. One larva was then placed on a chamber slide, containing 3% methylcellulose in E3 water, for fluorescent microscopy (Leica DM2500 microscope equipped with a DFC425 C digital camera). Images were captured at 50× magnification. The remaining 5 larvae where lysed with 120 µL of CelLytic M solution (Sigma-Aldrich) and sonication (4° C., 10"/5" pulse, 10 min). Lysed larvae were centrifuged at 10000 rpm for 10 min. 100 µL of the supernatant was transferred to a 96-well plate and fluorescence was measured with a fluorescent microplate reader (SpectraMAX Gemini XS, Molecular Devices; $\lambda_{ex}$=466 nm $\lambda_{ex}$=540 nm).

Statistics

The student's t test was used for comparison between experimental groups (Microsoft Excel, reference number 14.0.6023.1000). P values of less than 0.05 were considered to be significant. Unless otherwise stated, all presented results are representative of three independent experiments, which were carried out at different days.

Results

Identification of AP-III-a4 (ENOblock)

We developed a novel, dual screening system to identify molecules that preferentially kill cancer cells in a hypoxic environment (FIG. 1). A small molecule library of 384 triazines prepared on a solid support5 (5; FIG. 3) was screened. A "hit" molecule was defined as an inducer of at least 25% increased cancer cell toxicity in hypoxia compared to normoxia (as determined using the 3-(4,5-dimethylthiazol-2-yl)-2,5-diphenyltetrazolium bromide, a tetrazole (MTT) assay). Five from 384 triazines screened produced greater cancer cell toxicity under hypoxia. The best performing hit molecule was AP-III-a4(1; FIG. 1b). AP-III-a4 treatment of cancer cells cultured under hypoxia reduced cell viability dose-dependently (FIG. 1c-1d).

ENOblock Binds to Enolase and Inhibits Its Activity.

Figure 4A:
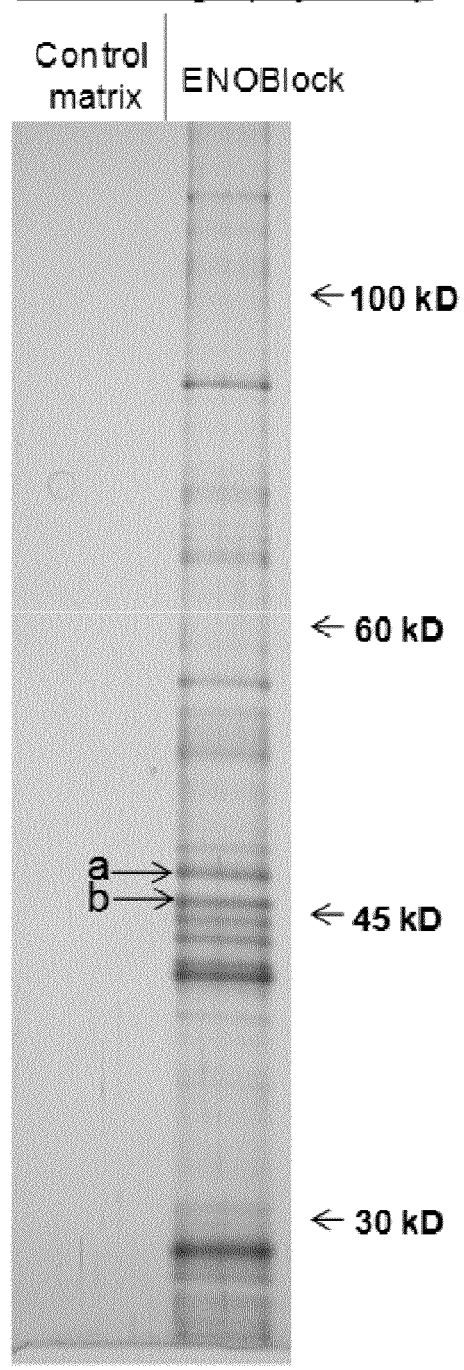
FIG. 4. Discovery that compound AP-III-a4 (ENOblock) is a direct inhibitor of enolase. (a) Affinity chromatography study for ENOblock in HCT116 cancer cells. Protein bands marked "a" and "b" were identified by mass spectrometry as subunits of the heterodimer, enolase. In contrast, mass spectrometry failed to identify the other prominent protein bands in the eluate from the ENOblock affinity matrix. Control matrix=AP-IV-e3 (2) affinity matrix, which showed no binding to HCT116 lysate proteins. (b) Sequence identification for the enolase monomer subunit. Identified peptides are shown in red. Mascot scores above 100 were deemed to be significant. (c) Western blot analysis confirmed that enolase in HCT116 cancer cell lysate binds to the ENOblock affinity matrix. Competition analysis using free ENOblock (abbreviated as ENO) as a competitor completely inhibited enolase binding to the ENOblock affinity matrix. Twenty micrograms of cell lysate from YD-10B oral cancer cells or Huh7 hepatocytes were used as positive controls. (d) Western blot analysis confirmed that purified human enolase binds to the ENOblock affinity matrix. Competition analysis using free ENOblock as a competitor inhibited purified enolase binding to the ENOblock affinity matrix. In contrast, the APIV-e3 control compound affinity matrix could not bind to the purified enolase. As a positive control, ENOblock affinity matrix was incubated with 200 µg of HCT 116 cell lysate; 50 µg cell lysate from HCT116 cancer cells was used as a positive control for the enolase antibody. (e) ENOblock dose-dependently inhibited the activity of purified enolase. ENOblock inhibited enolase activity at a markedly lower concentration than the wellknown enolase inhibitor, sodium fluoride (NaF); 2.5 µM ENOblock treatment reduced enolase activity to a level as approximated with 1 mM NaF treatment. Error=SD; *=P<0.05 compared to the untreated group. P value: Fluoride 0.5 mM=0.007708; Fluoride 1 mM=0.000543.
Figure 4D:
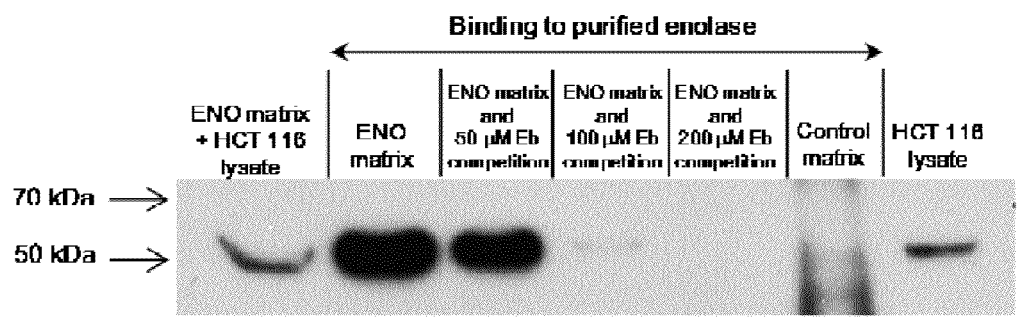
Figure 4E:
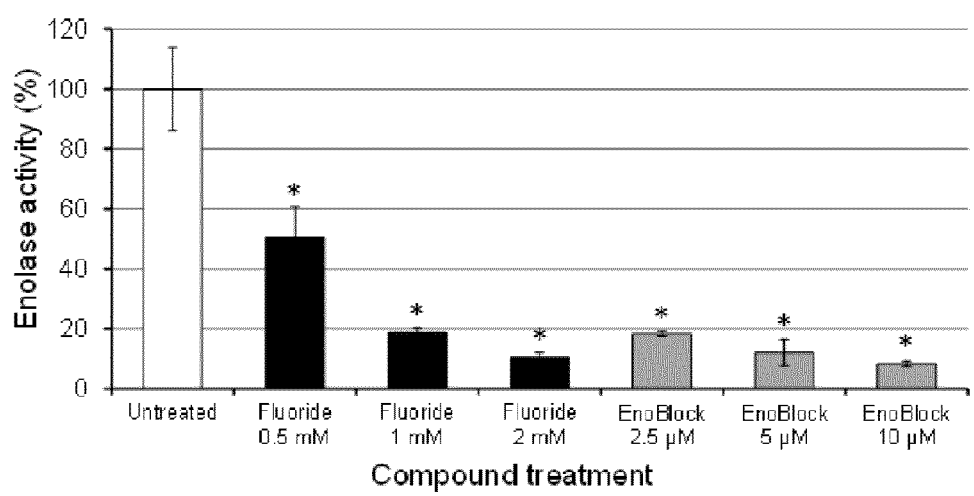

Affinity chromatography was used to identify the cellular target for AP-III-a4. Target identification strategies for the triazine library used in this study are relatively straightforward, because the molecules contain a built-in linker moiety. This allows conjugation to an affinity matrix with reduced risk of compromising biological activity. Silver staining of proteins eluted from the AP-III-a4 affinity matrix is shown in FIG. 4a. Mass spectrometry analysis revealed that two protein bands of approximately 45 kD mass were subunits of enolase, a glycolysis enzyme, and a protein band of approximately 40 kD was actin (FIG. 4b). Thus, we renamed molecule AP-IIIa4 "ENOblock". ENOblock binding to enolase in cancer cell lysates was confirmed by Western blot analysis of proteins eluted from the ENOblock affinity matrix. Competition analysis with free ENOblock inhibited enolase binding to the ENOblock affinity matrix (FIG. 4c). Moreover, ENOblock could bind to purified human enolase, suggesting a direct interaction between ENOblock and enolase (FIG. 4d). Subsequent analysis showed that enolase activity can be inhibited by ENOblock dose-dependently (FIG. 4e). As an additional control, we also tested another non-hit compound from the tagged triazine library, AP-I-f10 (3), which was shown to not reduce enolase activity (FIG. 5). To test that ENOblock treatment under hypoxia induced cytotoxicity, rather than inhibition of cell proliferation, siRNA-mediated enolase knock-down HCT1167 cancer cells were stained with trypan blue (FIG. 6). ENOblock-treated cells showed increased trypan blue uptake under hypoxia, which confirmed the induction of cell death.

ENOblock Inhibits Cancer Cell Migration and Invasion.

Figure 7A:
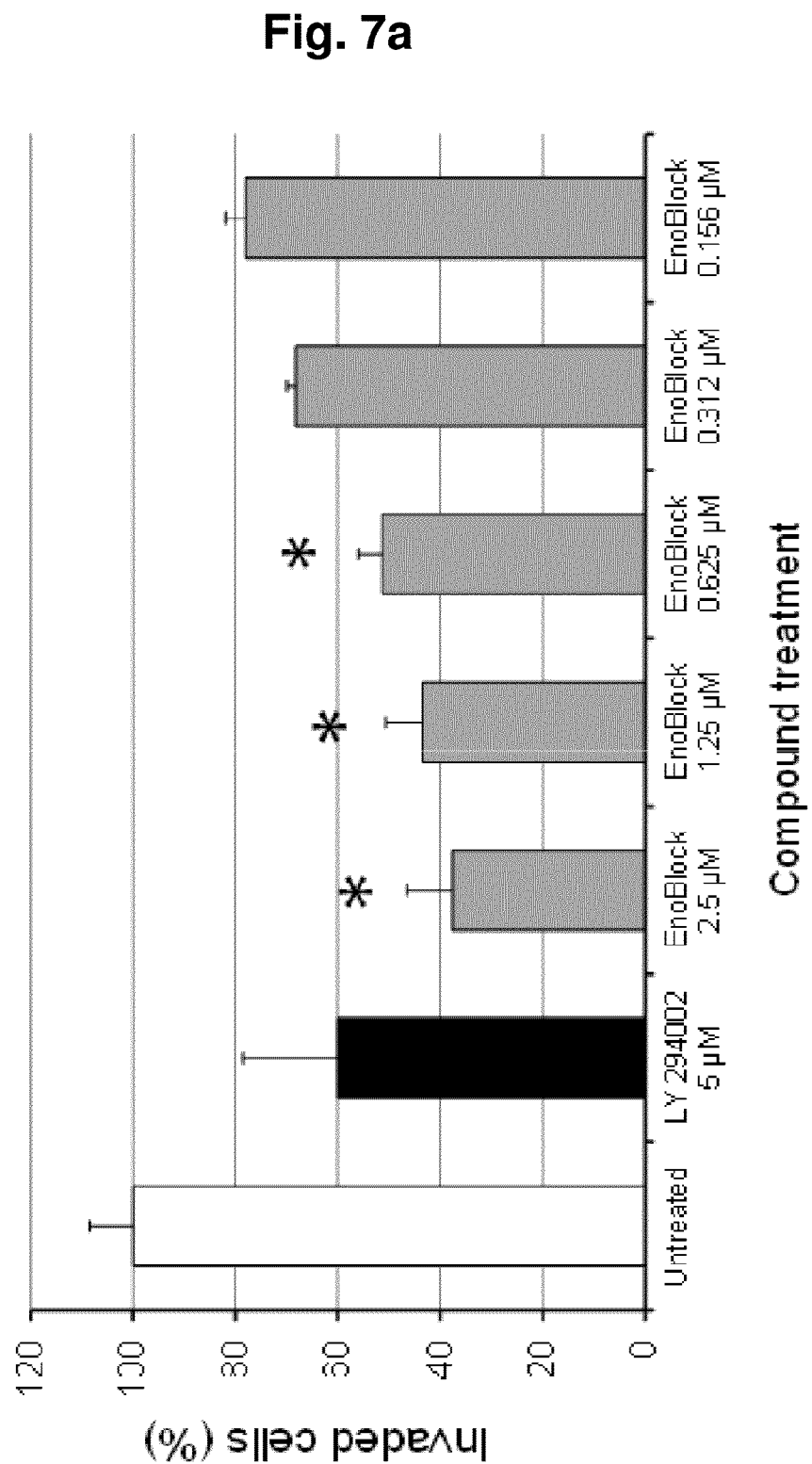
Figure 7B:
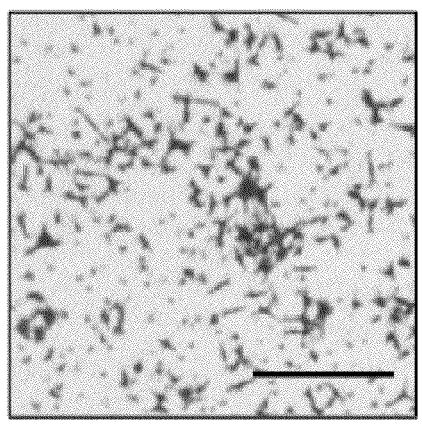
Figure 7B:
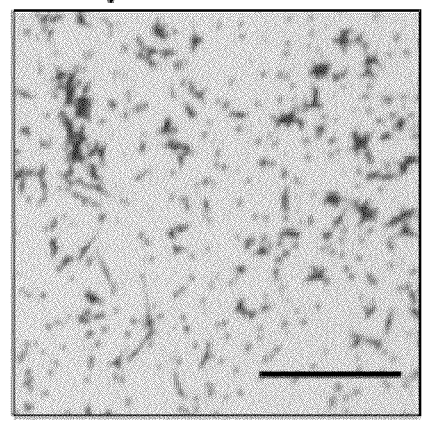
Figure 7B:
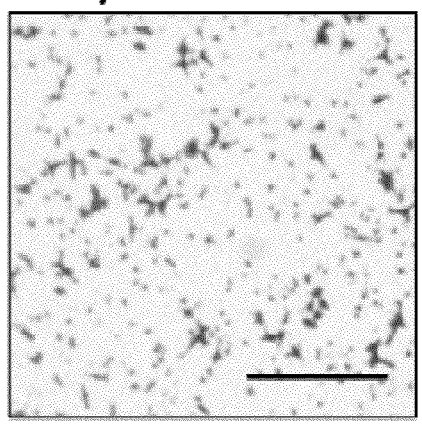
Figure 7B:
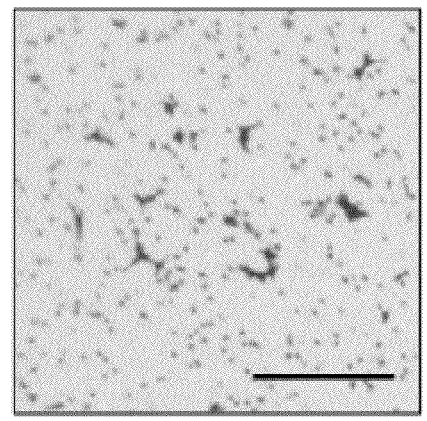
Figure 7C:
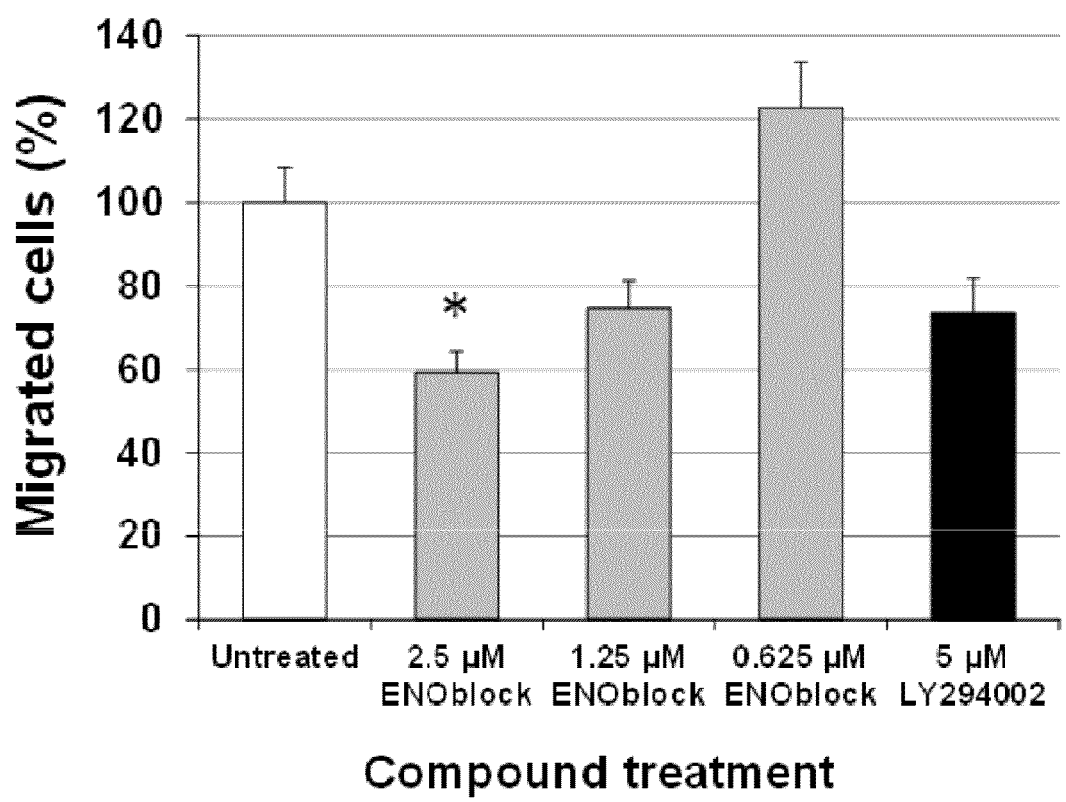
Figure 7D:
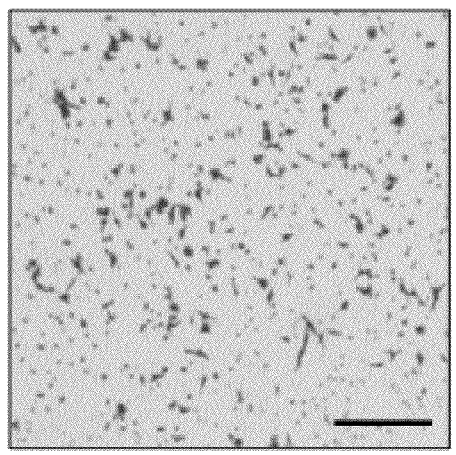
Figure 7D:
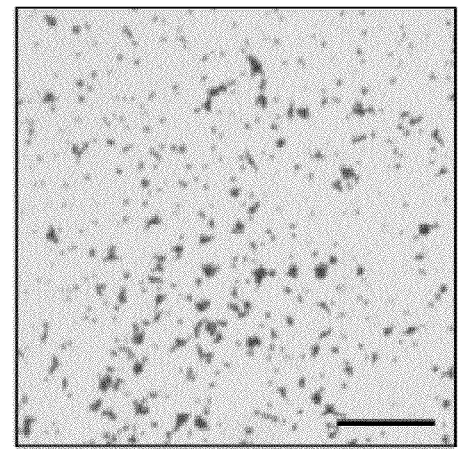
Figure 7D:
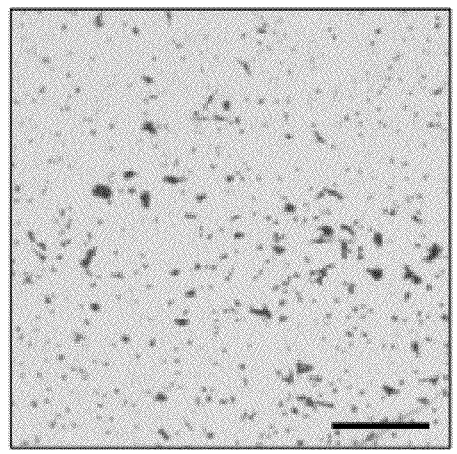
Figure 7D:
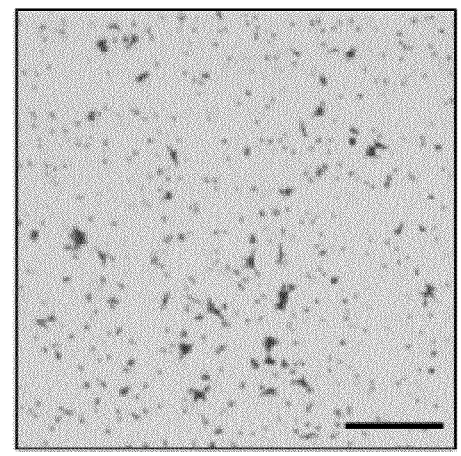
Figure 7E:
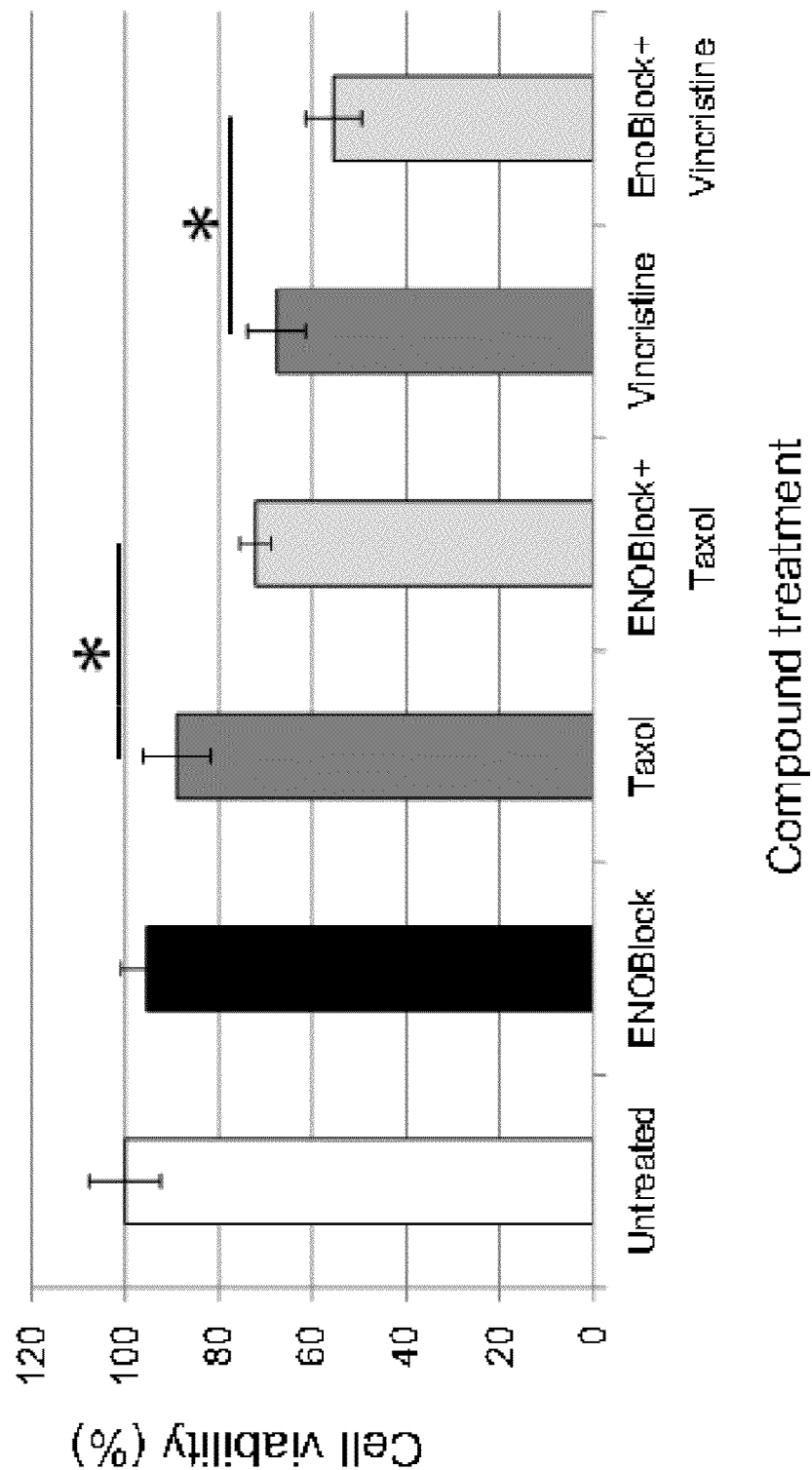
Figure 7F:
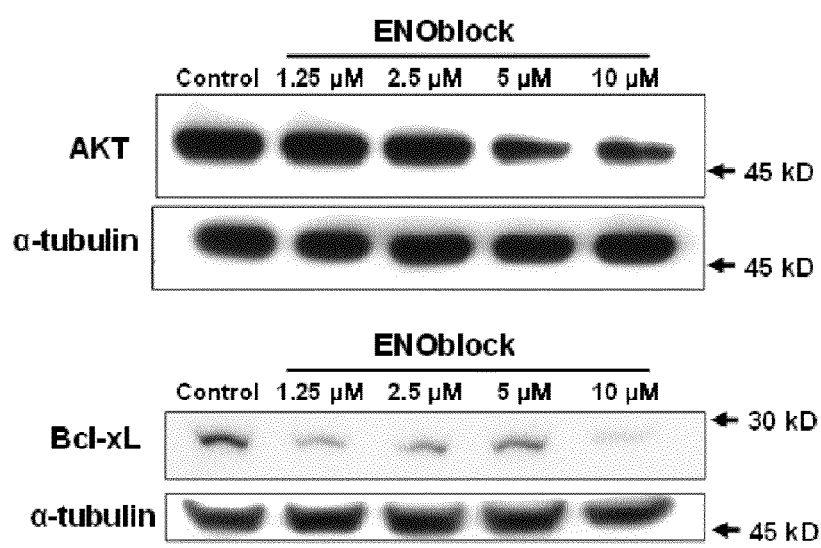

Enolase is a "moonlighting" metabolic enzyme, because it performs multiple functions that are unrelated to its innate glycolytic function.7,8 Thus, we speculated that ENOblock represents a powerful chemical tool to characterize the moonlighting functions of enolase. As our first test, we assessed the role of enolase in cancer progression (FIG. 7). We found that enolase inhibition by ENOblock can reduce cancer cell invasion, which to our knowledge is the first confirmation that enolase activity is linked to metastasis (FIGS. 7a-7b). As an additional control, we also tested another compound from the tagged triazine library, AP-I-f10 (3), which did not reduce cell invasion (FIG. 8). Moreover, ENOblock treatment also inhibited cancer cell migration (FIGS. 7c-7d). ENOblock treatment reduced cancer cell invasion/migration under normoxia at concentrations that do not induce cytotoxicity (compare FIGS. 7a-7b, with FIG. 1c). Previous studies have shown that enolase expression knockdown can increase cytotoxicity induced by the cancer drugs taxol and vincristine.9 In accordance with this finding, we observed that ENOblock treatment could also increase cancer cell cytotoxicity induced by taxol and vincristine (FIG. 7e). To investigate how ENOblock may induce cancer cell cytotoxicity, we measured the expression of two proteins that are linked to the induction of apoptosis, AKT10 and Bcl-xL.11 ENOblock treatment decreased the expression of AKT and BclxL (FIG. 7f).

Figure 9B:
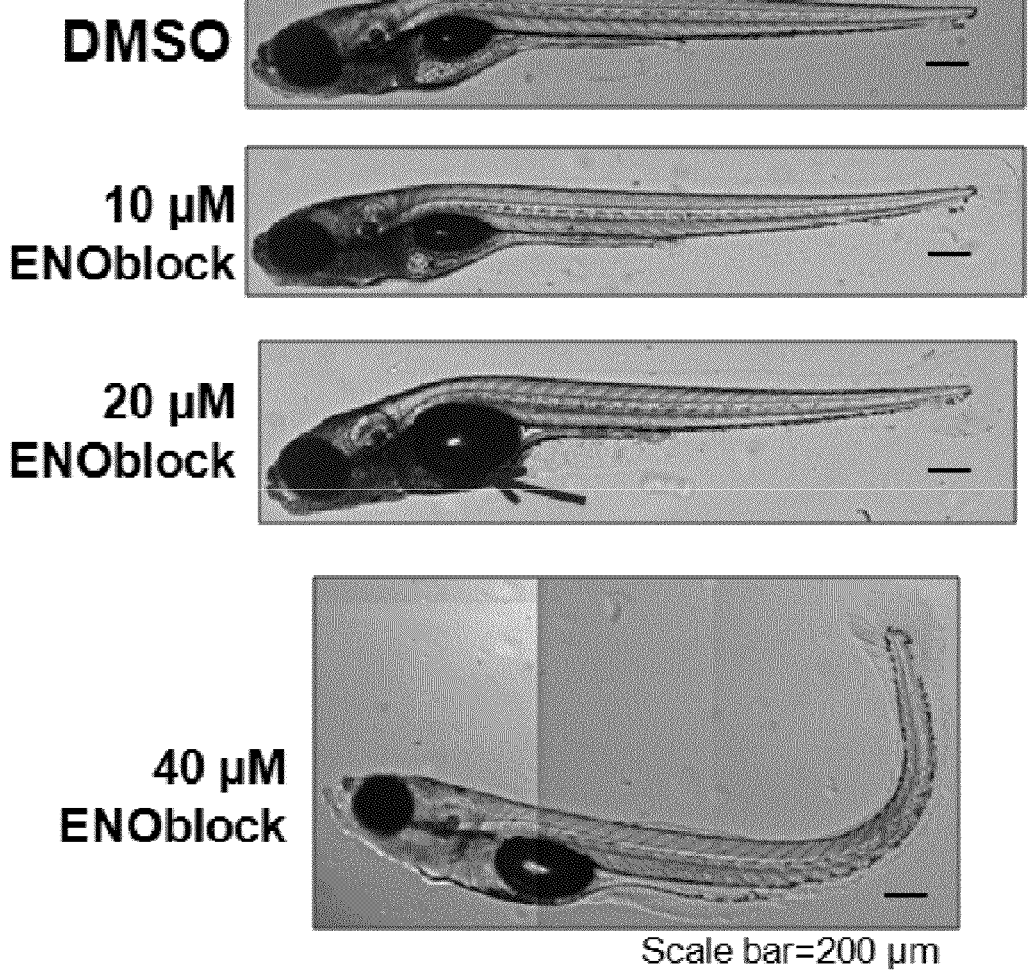
Figure 9C:
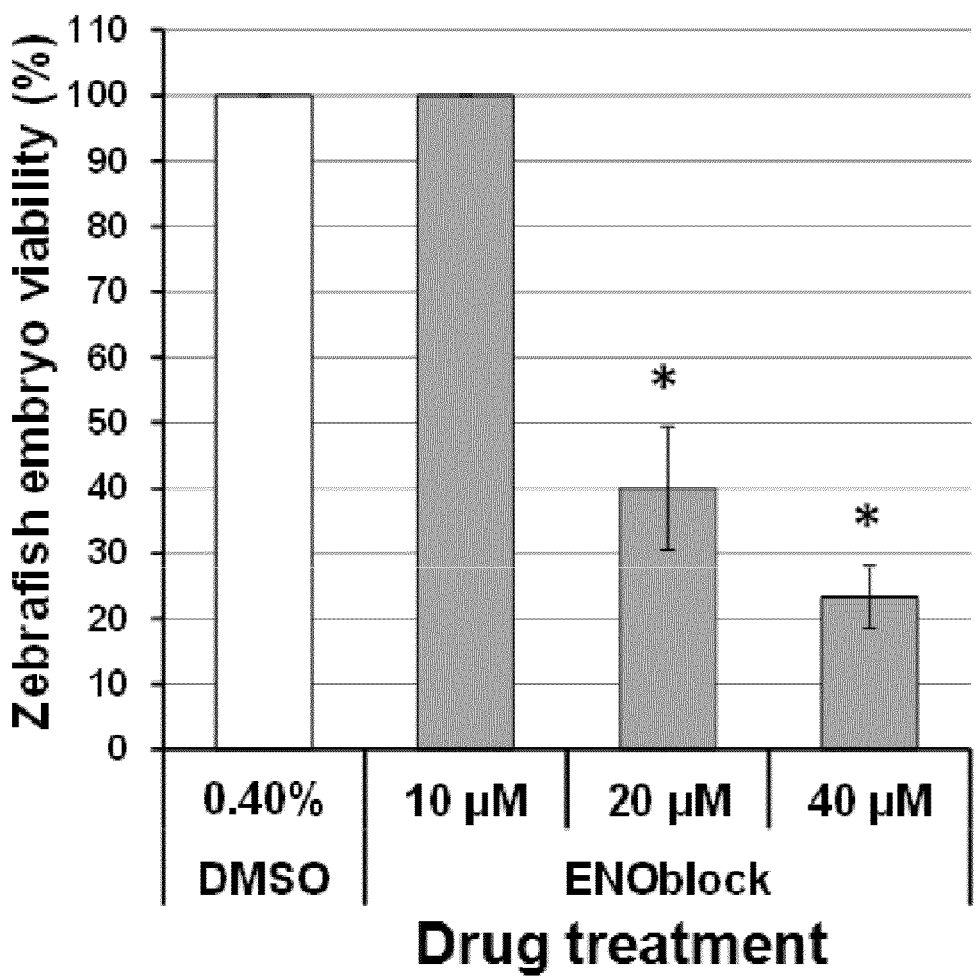
Figure 9D:
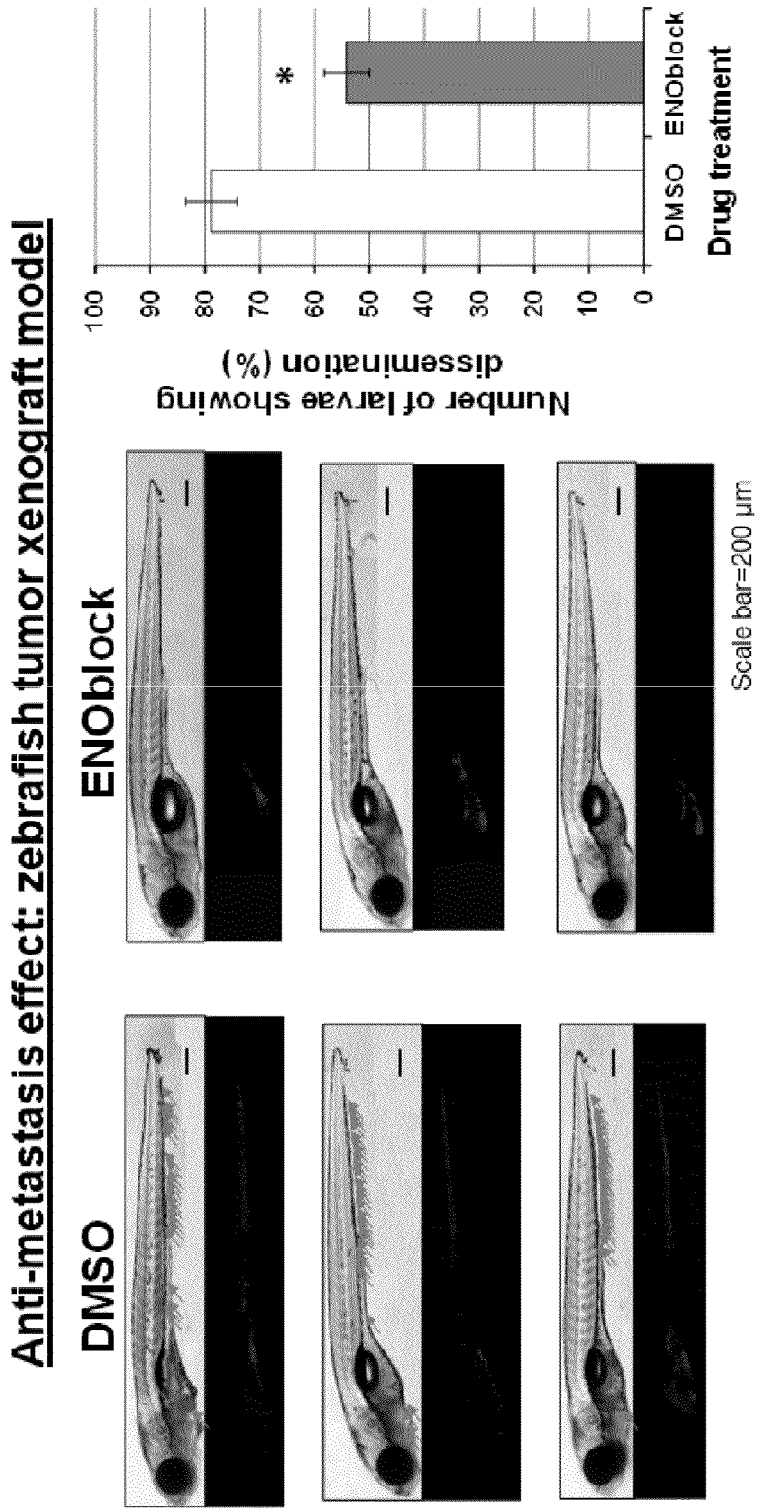

The zebrafish (Danio rerio) cancer cell xenograft model is gaining increasing research prominence as a validated, convenient tool for testing candidate cancer drugs in vivo.[10,11] In addition, zebrafish is a relevant vertebrate platform for predicting toxicological effects in mammals.[12] We observed that 10 µM ENOblock treatment of developing zebrafish larvae was nontoxic (FIG. 9a-9c). Employing a recently published zebrafish tumor xenograft model validated for anticancer drug testing,[10] we observed that ENOblock treatment reduced cancer cell dissemination, suggesting an inhibition of cancer cell migration and invasion processes (FIG. 9d).

ENOblock Induces Cellular Glucose Uptake and Down-regulates PEPCK Expression.

Figure 10A:
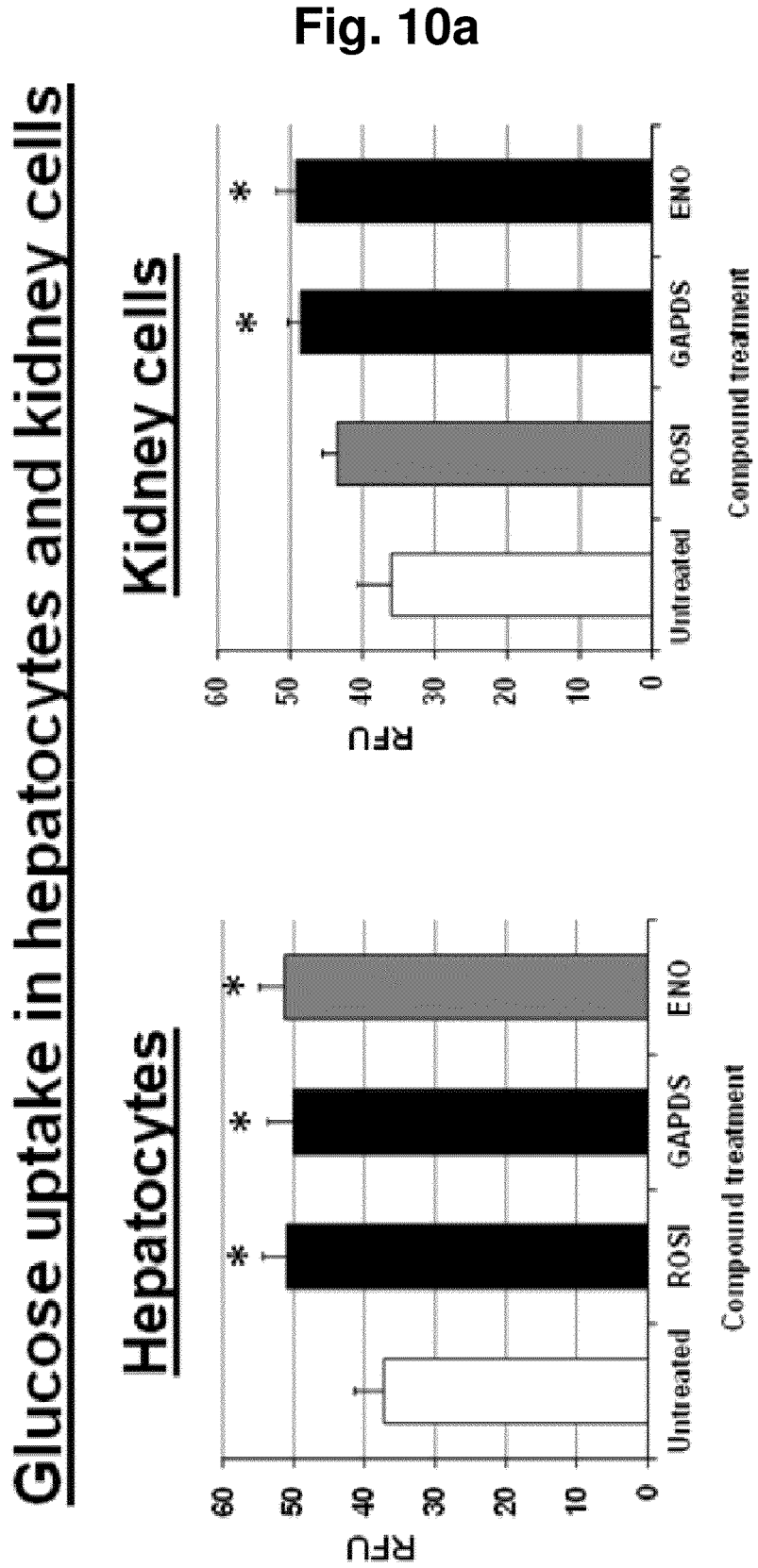

Interestingly, ENOblock (compound AP-III-a4) was among a group of triazines previously identified in a screen to discover novel modulators of glucose uptake,[13] although the mechanism of action was not characterized in that study. Thus, we confirmed the ability of ENOblock to increase glucose uptake in cells, using the fluorescent probe 2-(N-(7-nitrobenz-2-oxa-1,3-diazol-4-yl)-amino)-2-deoxyglucose (2-NBDG)[14], which can be used to monitor cellular glucose flux (FIG. 10a). To our knowledge, this is the first demonstration that modulation of enolase function is linked to increased glucose uptake. The role of enolase in promoting cellular glucose uptake was confirmed by siRNA-mediated knock-down of enolase expression (FIG. 11).

Figure 10B:
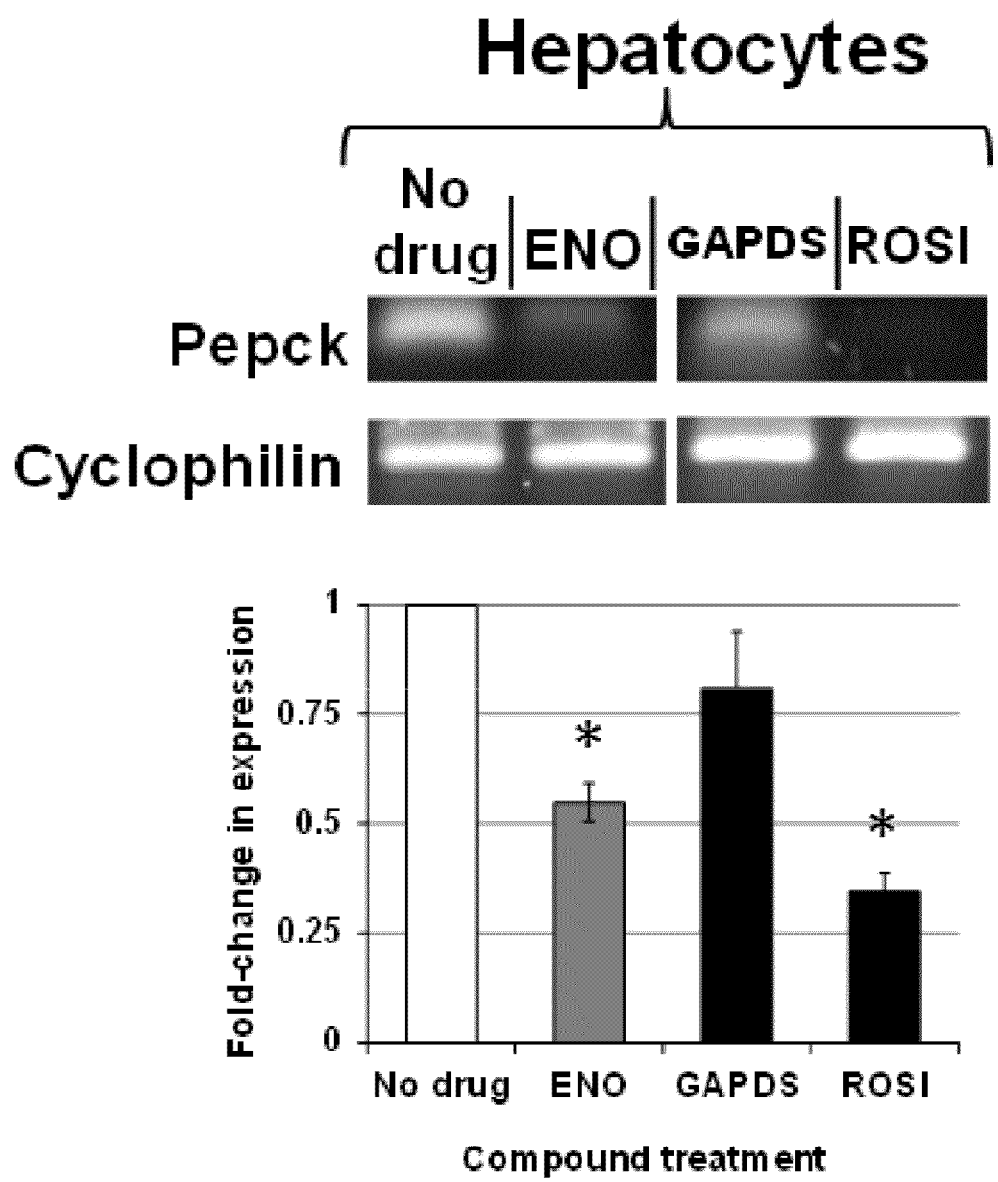
Figure 10C:
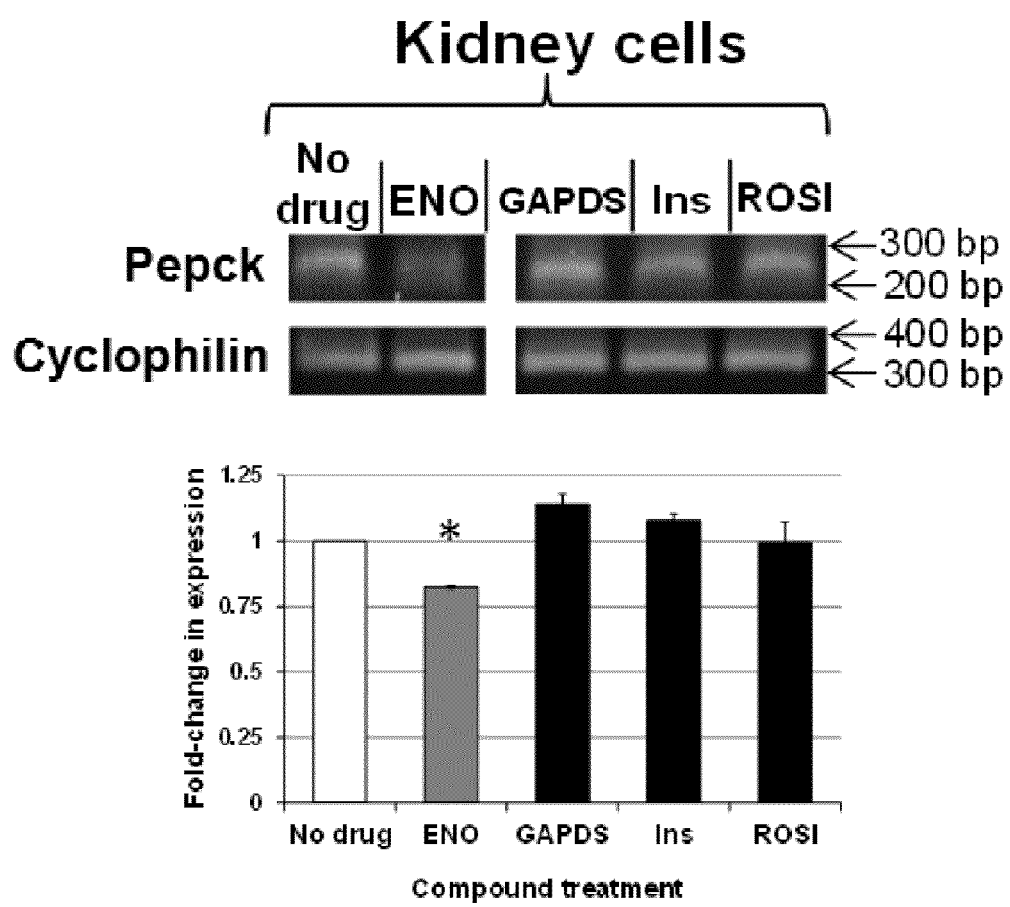
Figure 10D:
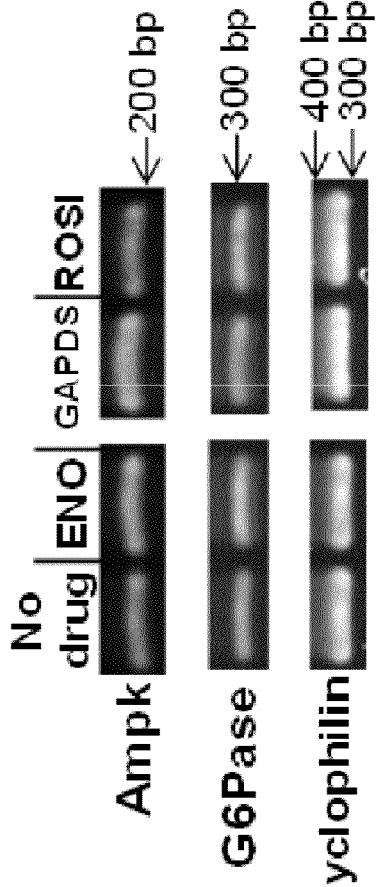
Figure 10D:
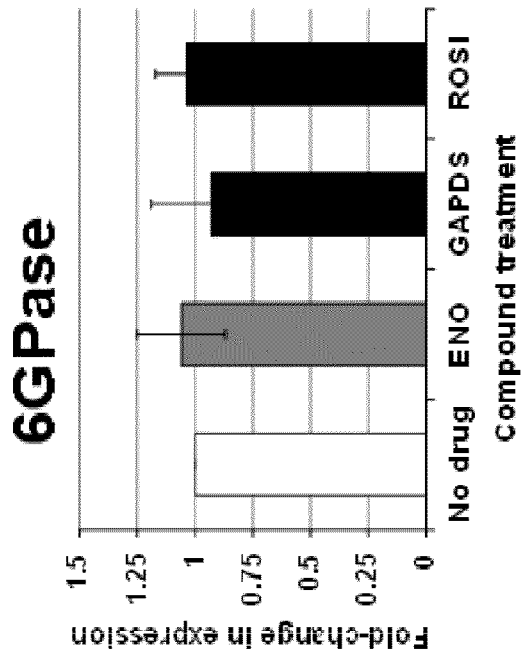
Figure 10D:
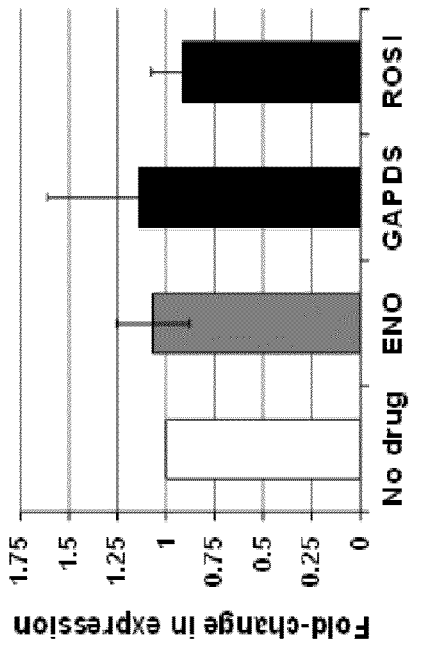

To characterize the mechanism by which ENOblock promotes glucose uptake, we assessed the expression of key enzymes linked to glucose homeostasis. We found that ENOblock down-regulates the expression of phosphoenolpyruvate carboxykinase (PEPCK) in hepatocytes, which catalyzes the rate-limiting step of liver tissue gluconeogenesis,[15] the process whereby glucose is synthesized (FIG. 9b). Of note, there is a precedent for the finding that small molecule regulation of a glycolysis enzyme regulates glucose uptake, with the report that GAPDS (4) targets glyceraldehyde 3-phosphate dehydrogenase (GAPDH) to promote glucose uptake (GAPDH catalyzes the sixth step of glycolysis, upstream of enolase).[16] Thus, we also measured PEPCK expression in hepatocytes after treatment with GAPDS or rosiglitazone (5), a well-known diabetes drug that can down-regulate PEPCK expression.[17] It was found that rosiglitazone can down-regulate PEPCK expression, while GAPDS had no effect, suggesting that GAPDS and ENOblock promote glucose uptake by different cellular mechanisms (FIG. 10b). Interestingly, the kidney is also a site of gluconeogenesis,[18] and it was observed that ENOblock treatment could also down-regulate PEPCK expression in kidney cells (FIG. 5c). In contrast, treatment of kidney cells with GAPDS, rosiglitazone, or insulin did not affect PEPCK expression (FIG. 10c). The enzyme glucose 6-phosphatase (G6 Pase) catalyzes the final step in gluconeogenesis plays a key role in the homeostatic regulation of glucose uptake by the liver.[19] We observed that ENOblock treatment of hepatocytes did not influence G6 Pase expression, which was also observed after treatment with GAPDS or rosiglitazone (FIG. 10d). The enzyme 5' AMPactivated protein kinase (AMPK) plays a key role in cellular energy homeostasis.[20] Similar to G6 Pase, we observed that treatment of hepatocytes with ENOblock, GAPDS, or rosiglitazone did not affect AMPK expression (FIG. 10d).

ENOblock Down-regulates PEPCK Expression and induces Glucose Uptake in Vivo.

Figure 12A:
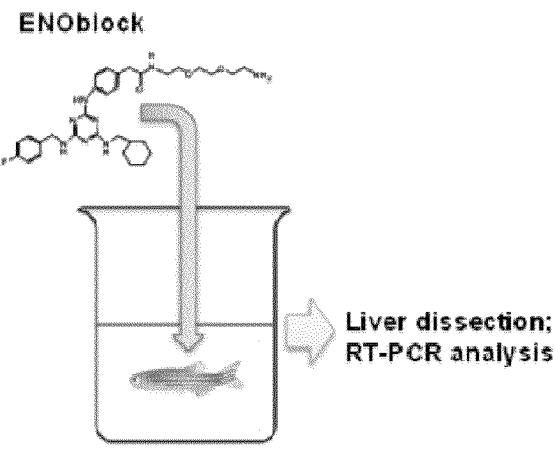
Figure 12B:
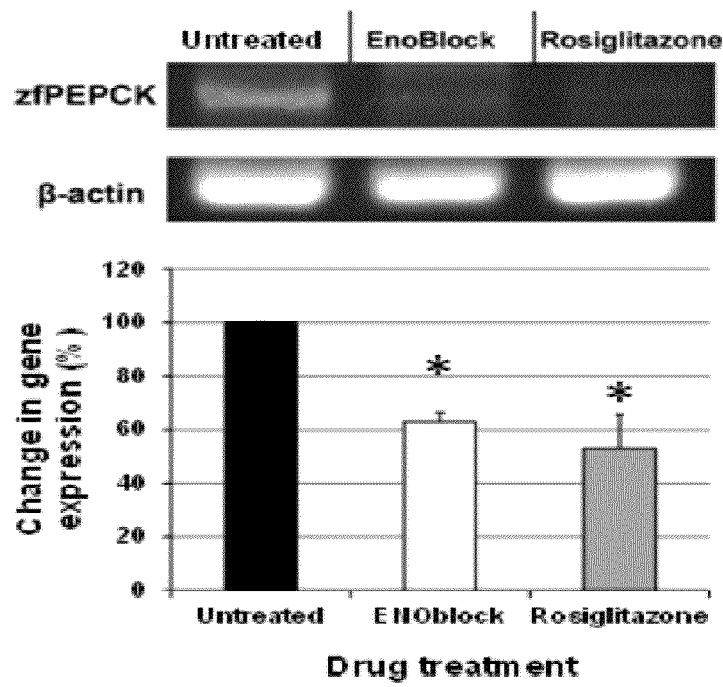
Figure 12C:
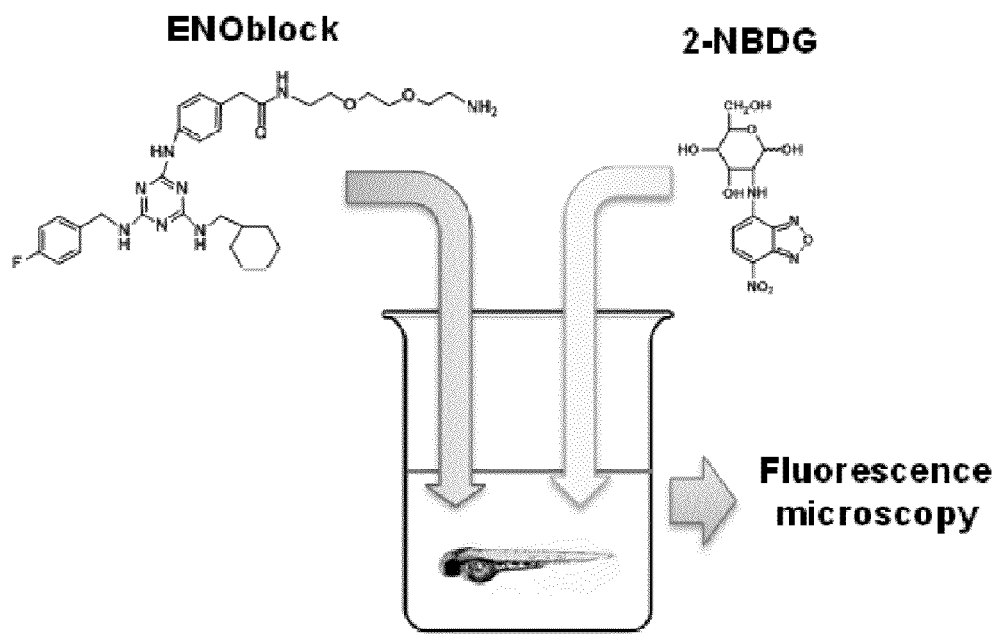
Figure 12D:
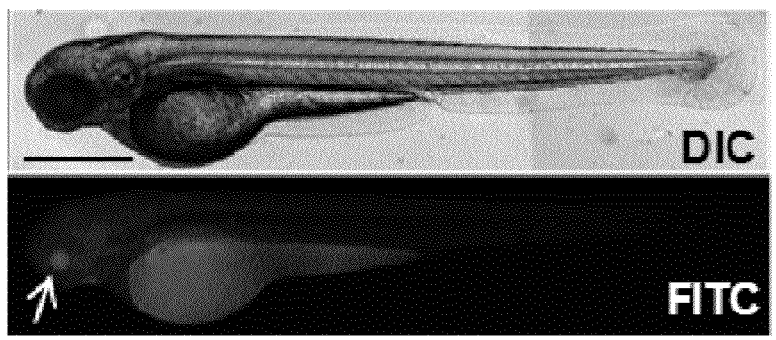
Figure 12D:
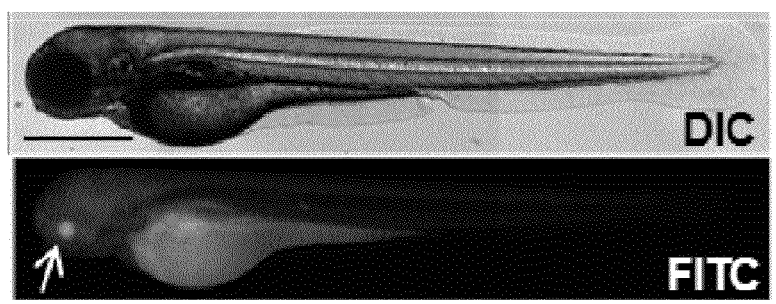
Figure 12D:
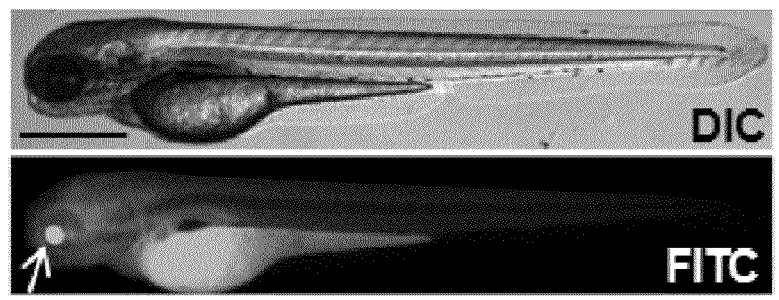
Figure 12E:
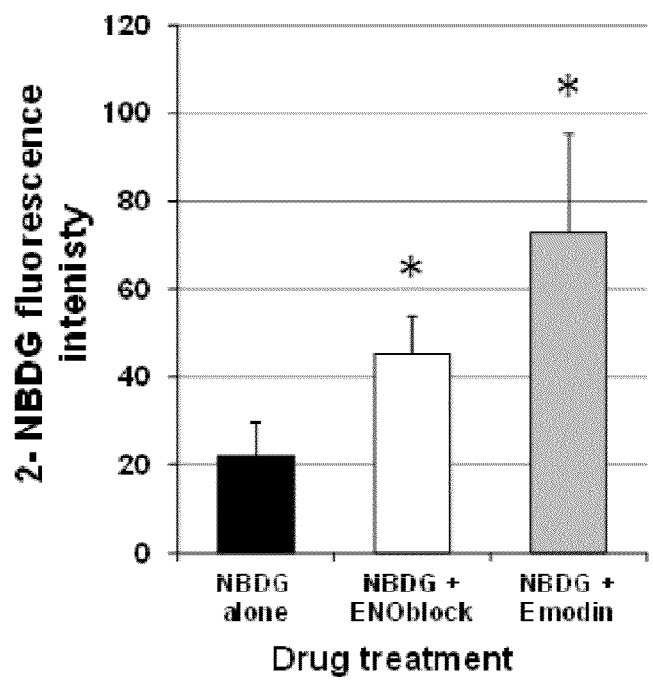

To investigate the effects of ENOblock on glucose homeostasis in vivo, we selected the zebrafish, because this animal model provides a convenient, rapid experimental format requiring small amounts of test compound. Moreover, it has been shown that zebrafish and mammals share similar glucose regulatory responses.[17,21] Adult zebrafish treated with ENOblock or rosiglitazone showed down-regulated hepatic PEPCK expression (FIGS. 12a-12b), which confirmed our cell-based findings. The fluorescent glucose probe 2-NBDG has been used to assess glucose uptake in zebrafish larvae, which are transparent and allow visualization of 2-NBDG fluorescence (e.g., ref 22). We observed that ENOblock treatment induced glucose uptake in zebrafish larvae (FIGS. 12c-12d). As a comparison, we also tested the effect of emodin (6-methyl-1,3,8-trihydroxyanthraquinone, a biologically active plant constituent that is known to promote cellular glucose uptake; 23). Fluorescence microscopy analysis of 2-NBDG treated larvae showed that emodin treatment increased glucose uptake (FIG. 12e). 2-NBDG uptake was quantified by measuring 2-NBDG fluorescence intensity in the zebrafish larvae eye at 72 hpf, because this tissue has been show to express a relatively large number of glucose transporter isoforms at this stage of development.[24] Image J anaylsis (National Institutes of Health, USA) confirmed that ENOblock or emodin treatment could promote glucose uptake in the zebrafish. 2-NBDG fluorescent signal in lysed larvae was measured using a fluorescent plate reader (FIG. 13). Results from this approach confirmed that ENOblock treatment induced glucose uptake in vivo.

ENOblock Treatment Inhibits Adipogenesis and Foam Cell Formation.

Figure 14A:
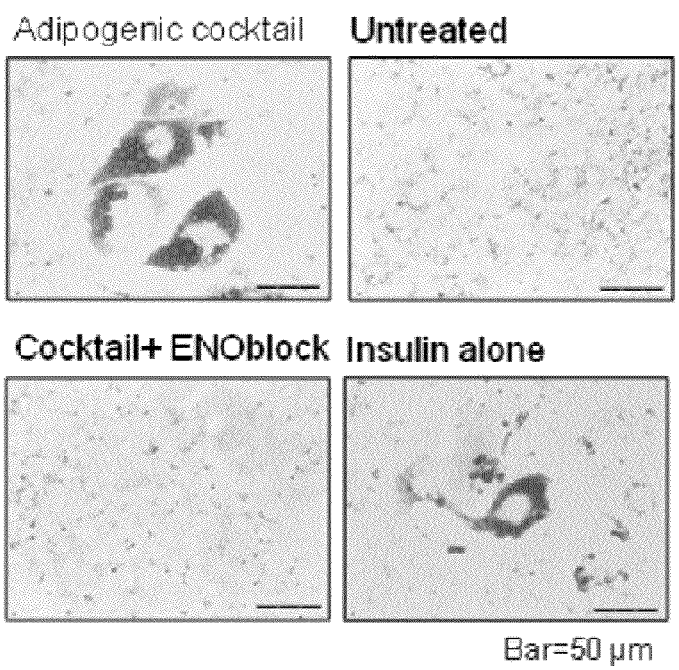
Figure 14A:
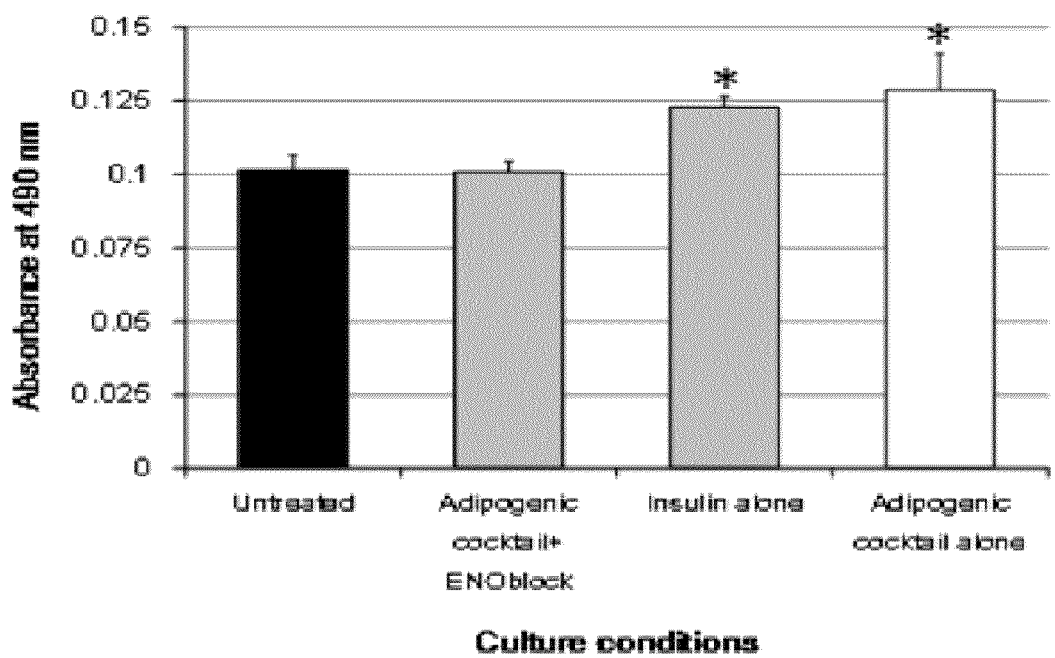
Figure 14B:
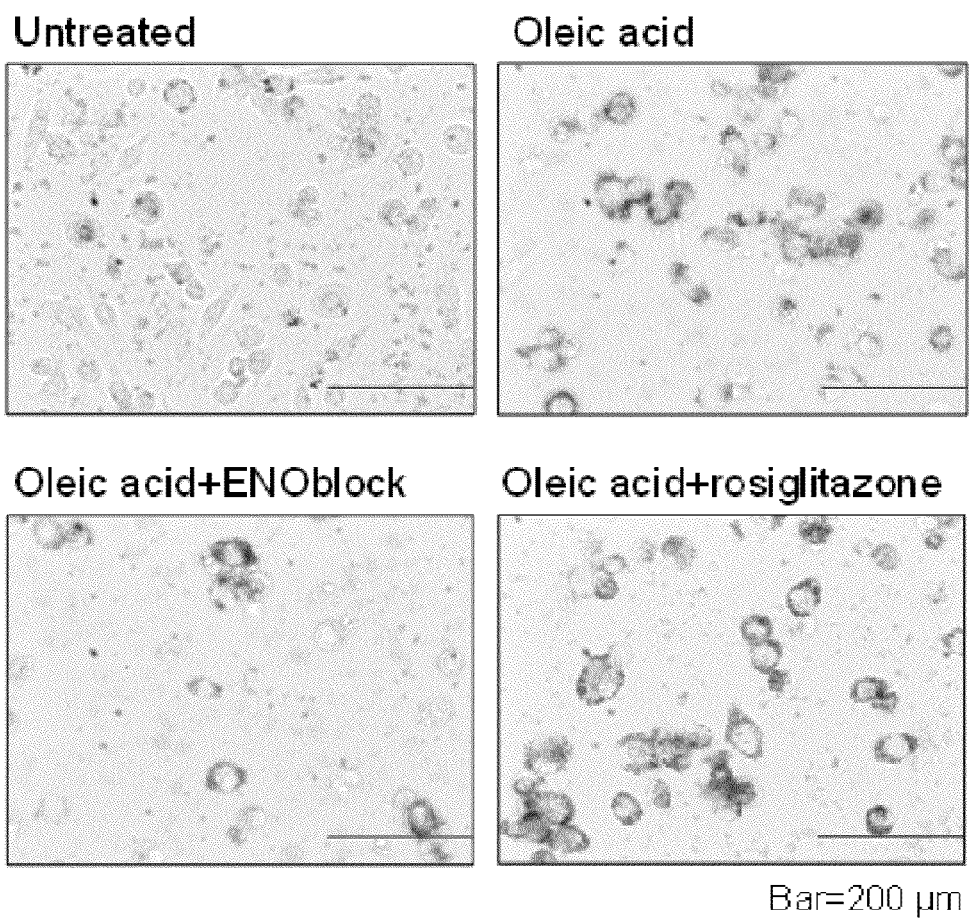
Figure 14C:
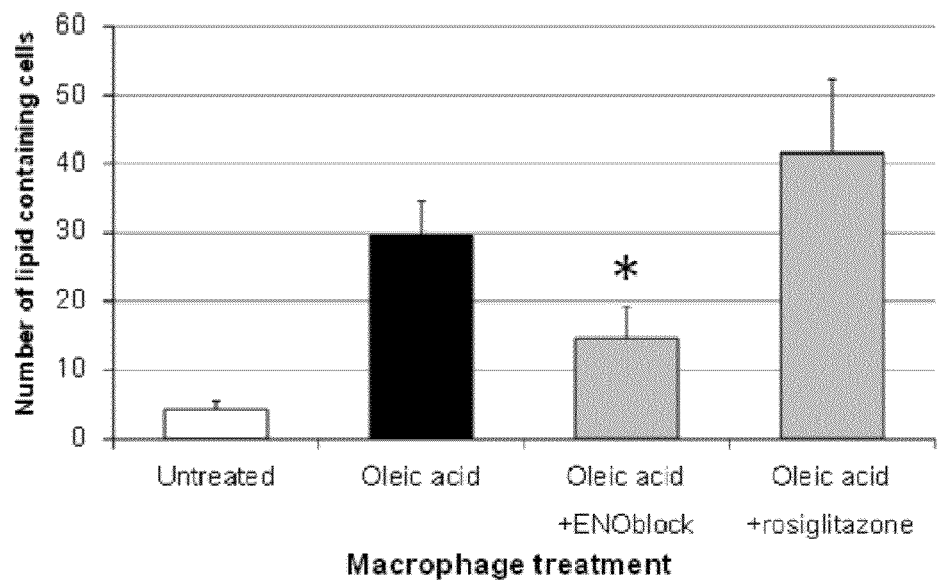
Figure 14D:
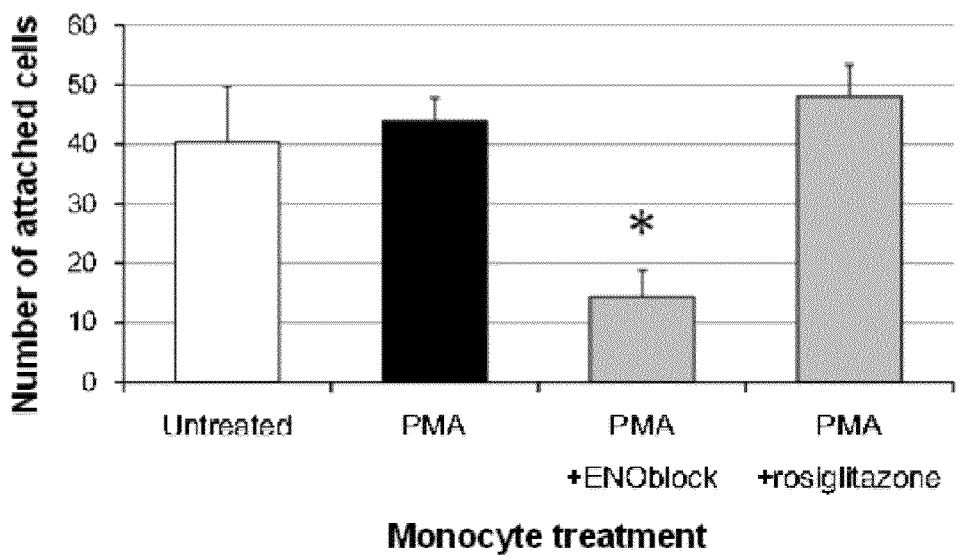
Figure 14E:
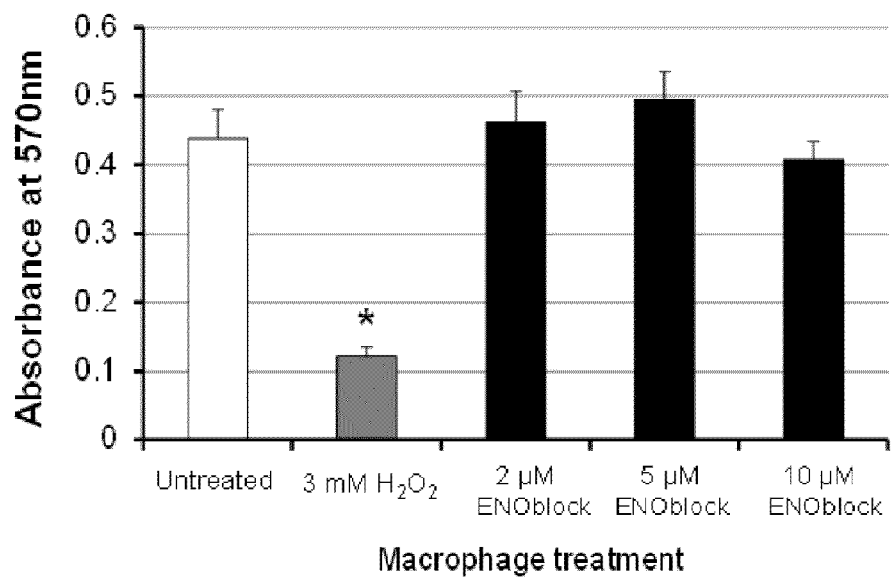

Commonly prescribed drugs for patients with diabetes are associated with side effects, such as weight gain or cardiovascular events.[25] Thus, we tested the effect of ENOblock on lipid accumulation in differentiating adipocyte precursor cells, which provides a convenient test for novel anti-obesity agents.[26] The positive effect of rosiglitazone on adipogenesis has already been described.[27] In contrast, we observed that ENOblock treatment inhibited lipid accumulation in adipocyte precursor cells exposed to adipogenic factors (FIG. 14a). Foam cell differentiation from macrophages adhered to blood vessel walls is a crucial step in the progression of atherosclerosis.[28] ENOblock treatment inhibited lipid accumulation in macrophages induced to undergo foam cell differentiation (FIG. 14b). Cell counting showed that ENOblock treatment inhibited both foam cell differentiation from macrophages and macrophage differentiation from monocytes (FIGS. 14c-14d). These inhibitory effects of ENOblock were observed at treatment concentrations that did not induce cytotoxicity (FIG. 14e).

Further Study

In this study, we describe a new small molecule, ENOblock, which is the first nonsubstrate analogue that directly binds to enolase and can be used as a probe to characterize enolase activity in biological systems. Enolase is a metalloenzyme that catalyzes the dehydration of 2-phospho-D-glycerate to phosphoenolpyruvate, which is the ninth and penultimate step of glycolysis.[6] Enolase also performs multiple functions that are unrelated to its innate glycolytic function.[1,6] To our knowledge, small molecule tools to clarify the diverse roles of enolase are rare. The most widely reported enolase inhibitor is phosphonoacetohydroxamate (PhAH). PhAH is thought to mimic the aci-carboxylate form of the intermediate carbanion in the reaction and is only applicable for crystallographic studies (e.g., ref 29, 30). Another two substrate analogues were developed, but these were only applied for direct spectrophotometric titration of the enolase active site and stopped-flow studies of enzyme kinetics (D-tartronate semialdehyde phosphate[34] and 3-aminoenolpyruvate phosphate[31,32]). Moreover, these substrate analogues are not commercially available. Inorganic sodium fluoride is also a substrate competitor for enolase. However, fluoride is not suitable for studying enolase in biological systems due to a variety of nonspecific toxic effects, such as phosphatase inhibition and the induction of increased oxidative stress or perturbed antioxidant defense mechanisms.[36,37] A recent report described the malaria drug mefloquine as an enolase inhibitor in *Schistosoma mansoni*.[34] However, mefloquine could not directly bind to recombinant enolase from this parasite and could not inhibit purified enolase activity. This suggests that, unlike ENOblock, mefloquine may not bind to enolase directly but exerts its effects via interacting with an uncharacterized enolase-modulating molecule in the cell extract. For example, it has been shown that enolase can bind to vacuoles or form large macromolecular complexes associated with mitochondria.[34] Thus, we propose that ENOblock is a powerful chemical tool to characterize the various, nonglycolytic 'moonlighting'[35] functions of enolase.

When discussing the activity of ENOblock, we believe that it is important to differentiate between the effects of this compound in hypoxic or normoxic conditions. We discovered ENOblock by screening for compounds that can induce greater levels of cancer cell death under hypoxia compared to normoxia. We adopted this approach because common cancer chemotherapy drugs are less effective under hypoxia.4 Our demonstration that enolase expression is rapidly up-regulated after the onset of hypoxia (FIG. 2) links the ability of ENOblock to kill cancer cells under hypoxia and its enolase inhibitory activity. Moreover, cancer cells are characterized by the Warburg effect, which is a group of metabolic alterations that increase reliance on anaerobic glycolysis for energy generation.[2] Thus, glycolysis inhibitors, such as 3-bromopyruvate and 6-aminonicotinamide, can kill cancer cells (reviewed in ref 3). In our study, we have shown that ENOblock selectively kills cancer cells under hypoxia (FIGS. 1c-1d), which is due to the glycolysis-related function of enolase (FIG. 6).

The multifunctional roles of enolase can also be probed using ENOblock under normoxia. For example, enolase is exported to the eukaryote cell surface via a nonclassical export pathway, and it has been suggested that enolase can mediate cancer cell invasion leading to metastasis.[36,37] We observed that ENOblock treatment of cancer cells under normoxia, at concentrations that are noncytotoxic, inhibited cancer cell invasion and migration (FIGS. 7a-7d). This finding suggests that ENOblock can also target cell-surface-bound enolase to modulate cancer cell metastasis. Our in vivo analysis of ENOblock treatment on metastasis was also carried out under normoxia, which showed that ENOblock can prevent cancer cell metastasis without noticeably affecting cancer cell viability (FIGS. 9d-9e; the cancer cells appear to be retained at the injection site without any reduction in cell numbers). Moreover, enolase has been shown to be associated with the cell microtubule system, which may negatively affect the efficacy of cancer drugs that disrupt microtubules.[7,38] Our results show that ENOblock treatment can increase the ability of microtubule-destabilizing drugs to kill cancer cells (FIG. 7e). Therefore, we speculate that ENOblock warrants further studies to assess its potential as a drug candidate for cancer therapy, because it can inhibit cancer cell metastasis and synergize with microtubule-destabilizing drugs under normoxia, while also possessing the potential to selectively kill cancer cells in hypoxic niches within tumors (cancer stem cells have been shown to express hypoxia-inducible factors that promote their survival under hypoxia (reviewed in ref 39).

Our study has also shown that enolase inhibition by ENOblock can induce cellular glucose uptake (FIG. 10a). Our results indicate that the ability of ENOblock to increase glucose uptake is due to a reduction of PEPCK expression. PEPCK expression has also been shown to be inhibited by insulin.[40] PEPCK inhibition in the liver reduces gluconeogenesis and concomitantly promotes glucose uptake.[15,41] Interestingly, gluconeogenesis in the kidney also plays a significant role in regulating blood glucose levels,[18] and our results show that ENOblock, but not insulin or the diabetes drug, rosiglitazone, can inhibit PEPCK expression in kidney cells (FIG. 10c). In addition, we have shown that enolase knock-down by siRNA can also induce glucose uptake (FIG. 15). Our demonstration that ENOblock treatment can inhibit PEPCK expression in vivo and induce glucose uptake suggests that ENOblock may be suitable for further studies to assess its potential as an anti-diabetes drug candidate. In support of this, is can be noted that enolase expression is increased in diabetic patients compared to normal subjects.[42] Moreover, our results suggest that ENOblock inhibits some of the complications associated with the use of diabetes drugs, such as increased adipogenesis and foam cell formation (FIG. 14). Insulin signaling is linked to accelerated foam cell formation,[43] and commonly prescribed diabetes drugs can induce adipogenesis or weight gain.[27] We believe that the ability of ENOblock to inhibit foam cell formation or adipogenesis further supports the potential of ENOblock to be developed as an anti-diabetic drug candidate. Interestingly, the most commonly prescribed antidiabetic drug, metformin, also inhibits hepatic gluconeogenesis and is currently the subject of various clinical trials as an anticancer drug (reviewed in ref 44).

To our knowledge, this study provides the first link between enolase inhibition and down-regulation of PEPCK expression, which inhibits gluconeogenesis. However, a precedent for this relationship exists in Nature. Studies in the mold *Aspergillus nidulans* have shown that, unexpectedly, mutation of the acuN gene (which encodes enolase) induces growth inhibition on gluconeogenic but not glycolytic carbon sources.[45] Therefore, we believe that further studies are warranted to assess the possible regulatory roles that other glycolysis enzymes exert over gluconeogenesis in mammals.

The in vivo analyses of ENOblock treatment presented herein have utilized the zebrafish vertebrate model. Zebrafish possess considerable advantages as the primary animal for testing novel therapeutic agents, such as (a) glucose homeostatic mechanisms that are conserved in mammals, (b) the availability of a validated cancer drug testing system, (c) toxicological responses that correlate with mammalian tests, and (d) the needs for relatively small amounts of test compound.[10,12,17,21,46] In addition, highly detailed studies of mammalian cell behavior can be carried out in zebrafish (e.g. ref 47). Therefore, we believe that our series of zebrafish-based analyses are a suitable format for the first report of ENOblock activity.

In summary, our study reports the small molecule ENOblock, which is the first nonsubstrate analogue inhibitor that directly binds to enolase and can be used to probe the various nonglycolytic functions of this enzyme. We have utilized ENOblock to assess the effect of enolase inhibition on cancer progression and show for the first time that enolase inhibition can reduce cancer cell metastasis in vivo. We also show for the first time that enolase inhibition can suppress the gluconeogenesis regulator PEPCK and is a new target for developing antidiabetic drugs. We believe that the discovery of ENOblock is a testament to the power of forward chemical genetics to provide new chemical probes, drug targets, and candidate therapeutics for previously uncharacterized cellular mechanisms regulating human disease. In light of the potential role of enolase in the pathogenesis of bacterial infections (such as *Yersinia pestis, Borrelia* spp., and *Streptococcus pneumonia*) and trypanosomatid parasites (reviewed in ref 48), in addition to the need to discover new glycolysis inhibitors for cancer therapy, we believe that ENOblock has the potential to make significant contributions to our understanding of these disorders.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

REFERENCES

1. Kim, J. W. and Dang, C. V., Multifaceted roles of glycolytic enzymes. Trends Biochem Sci 30 (3), 142 (2005).
2. Warburg, O., Wind, F., and Negelein, E., The Metabolism of Tumors in the Body. J Gen Physiol 8 (6), 519 (1927).
3. Pelicano, H., Martin, D. S., Xu, R. H., and Huang, P., Glycolysis inhibition for anticancer treatment. Oncogene 25 (34), 4633 (2006).
4. Xu, R. H. et al., Inhibition of glycolysis in cancer cells: a novel strategy to overcome drug resistance associated with mitochondrial respiratory defect and hypoxia. Cancer Res 65 (2), 613 (2005).
5. Khersonsky, S. M. et al., Facilitated forward chemical genetics using a tagged triazine library and zebrafish embryo screening. J Am Chem Soc 125 (39), 11804 (2003).
6. Pancholi, V., Multifunctional alpha-enolase: its role in diseases. Cell Mol Life Sci 58 (7), 902 (2001).
7. Georges, E., Bonneau, A. M., and Prinos, P., RNAi-mediated knockdown of alpha-enolase increases the sensitivity of tumor cells to antitubulin chemotherapeutics. Int J Biochem Mol Biol 2 (4), 303 (2011).
8. Kauffmann-Zeh, A. et al., Suppression of c-Myc-induced apoptosis by Ras signalling through PI(3)K and PKB. Nature 385 (6616), 544 (1997).
9. Boise, L. H. et al., bcl-x, a bcl-2-related gene that functions as a dominant regulator of apoptotic cell death. Cell 74 (4), 597 (1993).
10. Jung, D. W. et al., A novel zebrafish human tumor xenograft model validated for anti-cancer drug screening. Mol Biosyst 8 (7), 1930 (2012).
11. Corkery, D. P., Dellaire, G., and Berman, J. N., Leukaemia xenotransplantation in zebrafish—chemotherapy response assay in vivo. Br J Haematol 153 (6), 786 (2011).
12. Sipes, N. S., Padilla, S., and Knudsen, T. B., Zebrafish: as an integrative model for twenty-first century toxicity testing. Birth Defects Res C Embryo Today 93 (3), 256 (2011).
13. Jung, D. W. et al., Novel use of fluorescent glucose analogues to identify a new class of triazine-based insulin mimetics possessing useful secondary effects. Mol Biosyst 7 (2), 346 (2011).
14. Kim, W. H., Lee, J., Jung, D. W., and Williams, D. R., Visualizing sweetness: increasingly diverse applications for fluorescent-tagged glucose bioprobes and their recent structural modifications. Sensors (Basel) 12 (4), 5005 (2012).
15. Rosella, G. et al., Impaired suppression of gluconeogenesis induced by overexpression of a noninsulin-responsive phosphoenolpyruvate carboxykinase gene. Mol Endocrinol 7 (11), 1456 (1993).
16. Min, J. et al., Forward chemical genetic approach identifies new role for GAPDH in insulin signaling. Nat Chem Biol 3 (1), 55 (2007).
17. Elo, B., Villano, C. M., Govorko, D., and White, L. A., Larval zebrafish as a model for glucose metabolism: expression of phosphoenolpyruvate carboxykinase as a marker for exposure to anti-diabetic compounds. J Mol Endocrinol 38 (4), 433 (2007).
18. Mitrakou, A., Kidney: its impact on glucose homeostasis and hormonal regulation. Diabetes Res Clin Pract 93 Suppl 1, S66 (2011).
19. Hers, H. G., Mechanisms of blood glucose homeostasis. J Inherit Metab Dis 13 (4), 395 (1990).
20. Hardie, D. G. and Carling, D., The AMP-activated protein kinase—fuel gauge of the mammalian cell? Eur J Biochem 246 (2), 259 (1997).
21. Jurczyk, A. et al., Dynamic glucoregulation and mammalian-like responses to metabolic and developmental disruption in zebrafish. Gen Comp Endocrinol 170 (2), 334 (2011).
22. Jensen, P. J., Gunter, L. B., and Carayannopoulos, M. O., Akt2 modulates glucose availability and downstream apoptotic pathways during development. J Biol Chem 285 (23), 17673 (2010).
23. Yang, Y. et al., Emodin with PPARgamma ligand-binding activity promotes adipocyte differentiation and increases glucose uptake in 3T3-L1 cells. Biochem Biophys Res Commun 353 (2), 225 (2007).
24. Tseng, Y. C. et al., Specific expression and regulation of glucose transporters in zebrafish ionocytes. Am J Physiol Regul Integr Comp Physiol 297 (2), R275 (2009).
25. Agabegi, E D and Steven, S, Step-Up to Medicine (Step-Up Series). (Lippincott Williams & Wilkins, 2008).
26. Zeng, X. Y. et al., Screening for the efficacy on lipid accumulation in 3T3-L1 cells is an effective tool for the identification of new anti-diabetic compounds. Biochem Pharmacol (2012).
27. Madsen, L. et al., Adipocyte differentiation of 3T3-L1 preadipocytes is dependent on lipoxygenase activity during the initial stages of the differentiation process. Biochem J 375 (Pt 3), 539 (2003).
28. Chait, A., Progression of atherosclerosis: the cell biology. Eur Heart J 8 Suppl E, 15 (1987).
29. Zhang, E., Hatada, M., Brewer, J. M., and Lebioda, L., Catalytic metal ion binding in enolase: the crystal structure of an enolase-Mn2+-phosphonoacetohydroxamate complex at 2.4-A resolution. Biochemistry 33 (20), 6295 (1994).
30. Carmieli, R. et al., The catalytic Mn2+ sites in the enolase-inhibitor complex: crystallography, single-crystal EPR, and DFT calculations. J Am Chem Soc 129 (14), 4240 (2007).
31. Brewer, J. M., McKinnon, J. S., and Phillips, R. S., Stopped-flow studies of the reaction of D-tartronate semialdehyde-2-phosphate with human neuronal enolase and yeast enolase 1. FEBS Lett 584 (5), 979 (2010).
32. Spring, T. G. and Wold, F., Studies on two high-affinity enolase inhibitors. Reaction with enolases. Biochemistry 10 (25), 4655 (1971).
33. Mansour, H. H. and Tawfik, S. S., Efficacy of lycopene against fluoride toxicity in rats. Pharm Biol (2011).
34. Manneck, T., Keiser, J., and Muller, J., Mefloquine interferes with glycolysis in schistosomula of Schistosoma mansoni via inhibition of enolase. Parasitology 139 (4), 497 (2012).
35. Jeffery, C. J., Moonlighting proteins. Trends Biochem Sci 24 (1), 8 (1999).
36. Miles, L. A. et al., Role of cell-surface lysines in plasminogen binding to cells: identification of alpha-enolase as a candidate plasminogen receptor. Biochemistry 30 (6), 1682 (1991).
37. Liu, Ko-Jiunn and Shih, Neng-Yao, The Role of Enolase in Tissue Invasion and Metastasis of Pathogens and Tumor Cells. Journal of Cancer Molecules 3 (2), 45 (2007).
38. Walsh, J. L., Keith, T. J., and Knull, H. R., Glycolytic enzyme interactions with tubulin and microtubules. Biochim Biophys Acta 999 (1), 64 (1989).
39. Li, Z. and Rich, J. N., Hypoxia and hypoxia inducible factors in cancer stem cell maintenance. Curr Top Microbiol Immunol 345, 21 (2010).
40. O'Brien, R. M. et al., Identification of a sequence in the PEPCK gene that mediates a negative effect of insulin on transcription. Science 249 (4968), 533 (1990).
41. Quinn, P. G. and Yeagley, D., Insulin regulation of PEPCK gene expression: a model for rapid and reversible modulation. Curr Drug Targets Immune Endocr Metabol Disord 5 (4), 423 (2005).
42. Iori, E. et al., Glycolytic enzyme expression and pyruvate kinase activity in cultured fibroblasts from type 1 diabetic patients with and without nephropathy. Biochim Biophys Acta 1782 (11), 627 (2008).
43. Sekiya, M. et al., Ablation of neutral cholesterol ester hydrolase 1 accelerates atherosclerosis. Cell Metab 10 (3), 219 (2009).
44. Gallagher, E. J. and LeRoith, D., Diabetes, cancer, and metformin: connections of metabolism and cell proliferation. Ann N Y Acad Sci 1243, 54 (2011).
45. Hynes, M. J. et al., Transcriptional control of gluconeogenesis in Aspergillus nidulans. Genetics 176 (1), 139 (2007).
46. Selderslaghs, I. W., Blust, R., and Witters, H. E., Feasibility study of the zebrafish assay as an alternative method to screen for developmental toxicity and embryotoxicity using a training set of 27 compounds. Reprod Toxicol 33 (2), 142 (2012).
47. Zhu, S. et al., Activated ALK collaborates with MYCN in neuroblastoma pathogenesis. Cancer Cell 21 (3), 362 (2012).
48. Ghosh, A. K. and Jacobs-Lorena, M., Surface-expressed enolases of Plasmodium and other pathogens. Mem Inst Oswaldo Cruz 106 Suppl 1, 85 (2011).
49. Piret, J. P., Mottet, D., Raes, M., and Michiels, C., CoC12, a chemical inducer of hypoxia-inducible factor-1, and hypoxia reduce apoptotic cell death in hepatoma cell line HepG2. Ann N Y Acad Sci 973, 443 (2002).
50. Maher, J. C., Krishan, A., and Lampidis, T. J., Greater cell cycle inhibition and cytotoxicity induced by 2-deoxy-D-glucose in tumor cells treated under hypoxic vs aerobic conditions. Cancer Chemother Pharmacol 53 (2), 116 (2004).
51. Sedoris, K. C., Thomas, S. D., and Miller, D. M., Hypoxia induces differential translation of enolase/MBP-1. BMC Cancer 10, 157 (2010).
52. Gorsich, S. W., Barrows, V., Halbert, J., and Farrar, W. W., Purification and properties of gammagamma-enolase from pig brain. J Protein Chem 18 (1), 103 (1999).
53. Nusslein-Volhard, C and Dahm, R, Zebrafish: A Practical Approach (Practical Approach Series). (OUP, Oxford, 2002).

The invention claimed is:
1. A method for treating cancer, the method comprising administering to a subject a composition comprising: (a) a therapeutically effective amount of a triazine-based compound represented by chemical formula I below; and (b) a pharmaceutically acceptable carrier:

Chemical formula I

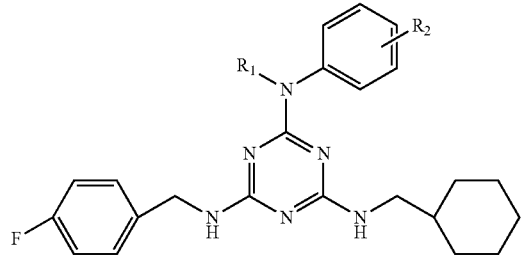

wherein in the chemical formula, $R_1$ is H or $C_1$-$C_5$ straight or branched chain alkyl; $R_2$ is H, $C_1$-$C_5$ straight or branched chain alkyl, $C_1$-$C_5$ straight or branched chain alkyl alcohol, —[(CH$_2$)$_m$—O]$_n$—(CH$_2$)$_p$—NH$_2$ (m, n, and p are each an integer of 1 to 10), —[(CH$_2$)$_m$—O]$_n$—CH$_3$ (m and n are each an integer of 1 to 10), —[(CH$_2$)$_m$—O]$_n$—(CH$_2$)$_p$—CpH$_3$ (m, n, and p are each an integer of 1 to 10), —(CH$_2$)$_q$—(CONN)—$C_{1-5}$ straight or branched chain alkyl (q is an integer of 0 to 5), —(CH$_2$)$_q$—(CONH)—$C_{1-5}$ straight or branched chain alkyl alcohol (q is an integer of 0 to 5), —(CH$_2$)$_q$—(CONN)—[(CH$_2$)$_m$—O]$_n$—(CH$_2$)$_p$—NH$_2$ (m, n, and p are each an integer of 1 to 10, and q is an integer of 0 to 5), —(CH$_2$)$_q$—(CONH)—[(CH$_2$)$_m$—O]$_n$—CH$_3$ (m and n are each an integer of 1 to 10, and q is an integer of 0 to 5), or —(CH$_2$)$_q$—(CONH)—[(CH$_2$)$_m$—O]$_n$—(CH$_2$)$_p$—CH$_3$ (m, n, and p are each an integer of 1 to 10, and q is an integer of 0 to 5).
2. The method of claim 1, wherein the triazine-based compound represented by chemical formula I is a compound represented by chemical formula II:

Chemical formula II

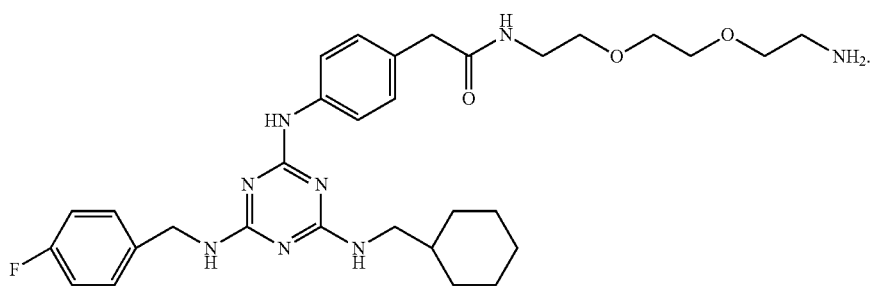

3. The method of claim 1, wherein the composition inhibits enolase activity.

4. The method of claim 1, wherein the composition inhibits cancer cell migration, invasion, and metastasis.

5. The method of claim 3, wherein the inhibition is further promoted in hypoxia conditions rather than normoxia conditions.

6. The method of claim 1, wherein the composition reduces the expression of apoptosis-inducible proteins.

7. The method of claim 6, wherein the apoptosis-inducible protein is AKT or Bcl-xL protein.

8. The method of claim 1, wherein the composition has insulin-mimicking activity.

9. The method of claim 8, wherein the insulin-mimicking activity promotes the intracellular glucose uptake.

10. The method of claim 1, wherein the composition down-regulates the expression of phosphoenolpyruvate carboxykinase (PEPCK).

11. The method of claim 1, wherein the composition inhibits adipogenesis and foam cell formation.

12. The method of claim 1, wherein the cancer is selected from the group consisting of brain cancer, neuroendocrine cancer, stomach cancer, lung cancer, breast cancer, ovarian cancer, liver cancer, bronchial cancer, nasopharyngeal cancer, laryngeal cancer, pancreatic cancer, bladder cancer, adrenal gland cancer, large intestine cancer, colon cancer, cervical cancer, prostate cancer, bone cancer, skin cancer, thyroid cancer, parathyroid cancer, and ureteral cancer.

13. A method for treating an enolase-associated disorder, the method comprising administering to a subject a composition comprising: (a) a therapeutically effective amount of a triazine-based compound represented by chemical formula I below; and (b) a pharmaceutically acceptable carrier:

Chemical formula I

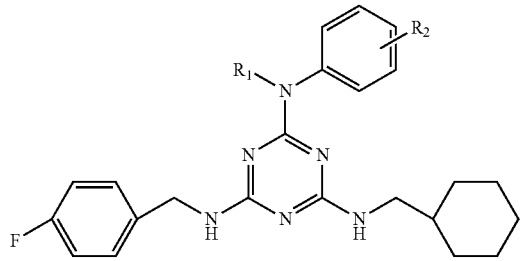

wherein in the chemical formula, $R_1$ is H or $C_1$-$C_5$ straight or branched chain alkyl; $R_2$ is H $C_1$-$C_5$ straight or branched chain alkyl, $C_1$-$C_5$ straight or branched chain alkyl alcohol, —[(CH$_2$)$_m$—O]$_n$—(CH$_2$)$_p$—NH$_2$ (m, n, and p are each an integer of 1 to 10), —[(CH$_2$)$_m$—O]$_n$—CH$_3$ (m and n are each an integer of 1 to 10), —[(CH$_2$)$_m$—O]$_n$—(CH$_2$)$_p$—CpH$_3$ (m, n, and p are each an integer of 1 to 10), —(CH$_2$)$_q$—(CONH)—C$_{1-5}$ straight or branched chain alkyl (q is an integer of 0 to 5), —(CH$_2$)$_q$—(CONH)—C$_{1-5}$ straight or branched chain alkyl alcohol (q is an integer of 0 to 5), —(CH$_2$)$_q$—(CONH)—[(CH$_2$)$_m$—O]$_n$—(CH$_2$)$_p$—NH$_2$ (m, n, and p are each an integer of 1 to 10, and q is an integer of 0 to 5), —(CH$_2$)$_q$—(CONH)—[(CH$_2$)$_m$—O]$_n$—CH$_3$ (m and n are each an integer of 1 to 10, and q is an integer of 0 to 5), or —(CH$_2$)$_q$—(CONH)—[(CH$_2$)$_m$—O]$_n$—(CH$_2$)$_p$—CH$_3$ (m, n, and p are each an integer of 1 to 10, and q is an integer of 0 to 5).

14. The method of claim 13, wherein the enolase-associated disorder is selected from the group consisting of autoimmune disorders, ischemia, and bacterial infection.

15. The method of claim 13, wherein the triazine-based compound represented by chemical formula I is a compound represented by chemical formula II:

Chemical formula II

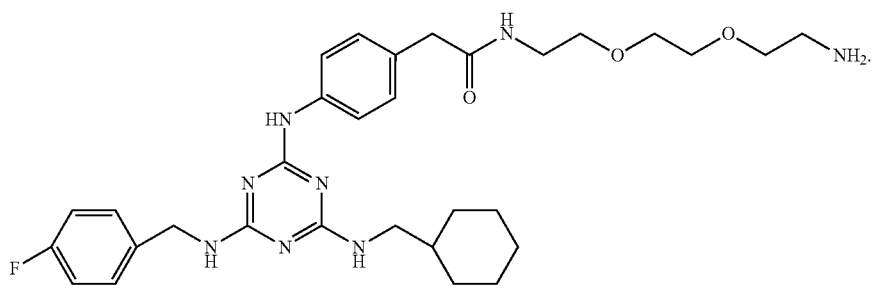

16. The method of claim 1, wherein the cancer is colon cancer.

17. The method of claim 1, wherein the cancer is lung cancer.

18. The method of claim 1, wherein the cancer is breast cancer.

19. The method of claim 1, wherein the cancer is prostate cancer.

20. The method of claim 13, wherein the enolase-associated disorder is an autoimmune disorder.

* * * * *